(12) United States Patent
Atsumi et al.

(10) Patent No.: US 9,701,948 B2
(45) Date of Patent: Jul. 11, 2017

(54) ESCHERICHIA COLI ENGINEERED FOR ISOBUTYRALDEHYDE PRODUCTION

(71) Applicant: The Regents of the University of California, Oakland, CA (US)

(72) Inventors: Shota Atsumi, Davis, CA (US); Gabriel Rodriguez, Davis, CA (US)

(73) Assignee: The Regents Of The University Of California, Oakland, CA (US)

( * ) Notice: Subject to any disclaimer, the term of this patent is extended or adjusted under 35 U.S.C. 154(b) by 57 days.

(21) Appl. No.: 14/408,941

(22) PCT Filed: Jun. 18, 2013

(86) PCT No.: PCT/US2013/046428
§ 371 (c)(1),
(2) Date: Dec. 17, 2014

(87) PCT Pub. No.: WO2013/192237
PCT Pub. Date: Dec. 27, 2013

(65) Prior Publication Data
US 2015/0322464 A1    Nov. 12, 2015

Related U.S. Application Data

(60) Provisional application No. 61/661,257, filed on Jun. 18, 2012.

(51) Int. Cl.
| | |
|---|---|
| *C12N 9/02* | (2006.01) |
| *C12N 1/20* | (2006.01) |
| *C12N 15/00* | (2006.01) |
| *C12N 9/04* | (2006.01) |
| *C12N 9/88* | (2006.01) |
| *C12P 7/24* | (2006.01) |

(52) U.S. Cl.
CPC .............. *C12N 9/0006* (2013.01); *C12N 9/88* (2013.01); *C12P 7/24* (2013.01); *C12Y 101/01001* (2013.01); *C12Y 101/01021* (2013.01); *C12Y 401/01001* (2013.01); *C12Y 401/01072* (2013.01); *C12Y 401/01074* (2013.01)

(58) Field of Classification Search
CPC ........ C12N 9/0004; C12N 15/00; C12N 1/20; C12Y 101/01001; C12Y 101/01002
See application file for complete search history.

(56) References Cited

U.S. PATENT DOCUMENTS

| | | |
|---|---|---|
| 2009/0047719 A1 | 2/2009 | Burgard et al. |
| 2009/0111154 A1 | 4/2009 | Liao et al. |
| 2010/0093044 A1* | 4/2010 | Terashita ............. C12N 9/0008 435/108 |
| 2011/0076733 A1 | 3/2011 | Urano et al. |
| 2011/0250660 A1* | 10/2011 | Liao ........................ C12N 1/20 435/147 |
| 2011/0262982 A1 | 10/2011 | Liao et al. |
| 2014/0065697 A1* | 3/2014 | Zhang ..................... C12N 1/20 435/252.33 |

FOREIGN PATENT DOCUMENTS

| | | |
|---|---|---|
| WO | 2010101665 A1 | 9/2010 |
| WO | 2012125688 A2 | 9/2012 |

OTHER PUBLICATIONS

Zhou J. (2011) "Alcohol Dehydrogenases Deletion to Increase Yield of Isobutyrate", Retrieved from the University of Minnesota Digital Conservancy, http://hdl.handle.net/11299/115503, pp. 1-11.*
Zhou J. (2016) http://conservancy.umn.edu/handle/11299/115503, pp. 1-3. This reference provides evidence that article "Alcohol Dehydrogenases Deletion to Increase Yield of Isobutyrate" by Zhou Jun is published on 2011.*
Atsumi et al., "Acetolactate Synthase from Bacillus Subtilis Serves as a 2-Ketoisovalerate Decarboxylase for Isobutanol Biosynthesis in *Escherichia coli*", Applied and Environmental Microbiology, vol. 75, No. 19, Oct. 2009, pp. 6306-6311.
Atsumi et al., "Direct Photosynthetic Recycling of Carbon Dioxide to Isobutyraldehyde", Nature Biotechnology, vol. 27, No. 12, Nov. 2009, pp. 1177-1180.
Atsumi et al., "Engineering the Isobutanol Biosynthetic Pathway in *Escherichia coli* by Comparison of Three Aldehyde Reductase/Alcohol Dehydrogenase Genes", Applied Microbiology and Biotechnology, vol. 85, Jan. 2010, pp. 651-657.
Atsumi et al., "Non-Fermentative Pathways for Synthesis of Branched-Chain Higher Alcohols as Biofuels", Nature, vol. 451, Jan. 2008, pp. 86-89.
Baba et al., "Construction of *Escherichia coli* K-12 in-Frame, Single-Gene Knockout Mutants: The Keio Collection", Molecular Systems Biology, 2006, pp. 1-11.
Rodriguez et al., "Isobutyraldehyde Production from *Escherichia coli* by Removing Aldehyde Reductase Activity", Microbial Cell Factories, vol. 11, No. 90, Jun. 2012, pp. 1-11.
Trinh et al., "Redesigning *Escherichia coli* Metabolism for Anaerobic Production of Isobutanol", Applied and Environment Microbiology, vol. 77, No. 14, Jul. 2011, pp. 4894-4904.
International Preliminary Report on Patentability received for PCT Patent Application No. PCT/US2013/046428, mailed on Dec. 31, 2014, 6 pages.
International Search Report and Written Opinion received for PCT Patent Application No. PCT/US2013/046428, mailed on Aug. 27, 2013, 7 pages.

* cited by examiner

Primary Examiner — Anand Desai
Assistant Examiner — Samuel Liu
(74) Attorney, Agent, or Firm — Morrison & Foerster LLP

(57) ABSTRACT

The present disclosure provides recombinant *E. coli* and other bacteria with reduced alcohol dehydrogenase and/or aldehyde reductase activity. The present disclosure further provides recombinant *E. coli* and other bacteria with reduced isobutyraldehyde reductase activity. Methods for the production and the uses of the recombinant bacteria are also provided. Specifically, recombinant bacteria further expressing 2-keto-acid decarboxylase can be used for producing higher aldehydes or other non-alcohol chemicals derived from aldehydes.

18 Claims, 16 Drawing Sheets

ESCHERICHIA COLI ENGINEERED FOR ISOBUTYRALDEHYDE PRODUCTION

CROSS-REFERENCE TO RELATED APPLICATION(S)

This application is a U.S. National Phase of PCT/US2013/046428, filed Jun. 18, 2013, which claims the benefit under 35 USC 119(e) of U.S. Provisional Application No. 61/661,257, filed Jun. 18, 2012, each of which is hereby incorporated by reference in its entirety.

FIELD OF THE INVENTION

The present disclosure provides recombinant *Escherichia coli* and other bacteria with reduced alcohol dehydrogenase and/or aldehyde reductase activity. The present disclosure further provides recombinant *E. coli* and other bacteria with reduced isobutyraldehyde reductase activity. Methods for the production and the uses of these recombinant bacteria are also provided.

BACKGROUND OF THE INVENTION

Long term economic and environmental concerns with the current petroleum-based economy have driven the development of approaches that convert renewable sources to organic chemicals to replace those derived from petroleum feed stocks. Production of biofuels, such as ethanol or butanol, through microorganisms has been a research focus in recent years and significant progress has been made in this area. At the same time, there remains a great need for development of biorefining processes that utilize microorganisms to convert renewable sources into industrially useful non-alcohol chemicals.

Aldehydes, in particular, are in great demand because they are usually quite reactive and can serve as building blocks or precursors for other chemicals. For example, isobutyraldehyde can be used to produce isobutanol, isobutyric acid, acetal and oxime, for various industrial purposes. Many microorganisms, such as *E. coli*, can convert aldehydes to alcohols through alcohol dehydrogenases (ADHs). However, due to the robust endogenous alcohol dehydrogenase and/or aldehyde reductase activity, aldehydes are efficiently converted to alcohols in *E. coli* with intact ADHs, and the natural net production of aldehydes or non-alcohol aldehyde derivatives, such as carboxylic acids, is usually low.

Isobutyraldehyde, in particular, is an important commodity chemical; it serves as a type of fragrance and can be used as a flavor additive, as well as in the production of plasticizers. Many microorganisms, such as *E. coli*, robustly convert aldehydes, such as isobutyraldehyde, into alcohols via alcohol dehydrogenase and/or aldehyde reductase activity. Isobutyraldehyde is converted to isobutanol via the action of isobutyraldehyde reductase (IBR) activity. Isobutyraldehyde reductase belongs to the broad class of alcohol dehydrogenase enzymes.

In view of these facts and the growing global demand for non-alcohol chemicals produced from renewable sources, a significant need exists for more productive recombinant microorganisms and improved methods for synthesis of these chemicals. Specially, recombinant *E. coli* and other bacteria are needed for cost-efficient biosynthesis of aldehydes and other non-alcohol chemicals that can be further derived from aldehydes.

BRIEF SUMMARY OF THE INVENTION

Provided herein are recombinant *E. coli* and other bacteria with substantially reduced alcohol dehydrogenase (ADH) and/or aldehyde reductase activity for the production of non-alcohol chemicals. Further provided are recombinant *E. coli* and other bacteria with substantially reduced isobutyraldehyde reductase activity (IBR) for the production of non-alcohol chemicals. Also provided are methods of using the recombinant bacteria to produce non-alcohol chemicals from suitable carbon sources.

In particular, the present disclosure provides an *E. coli* comprising a mutation in each of: (a) adhE, yqhD, adhP, eutG, yiaY, and yjgB genes, wherein the mutation reduces alcohol dehydrogenase activity of products of the genes; or (b) adhE, yqhD, adhP, eutG, fucO, and yjgB genes, and wherein the mutation reduces isobutyraldehyde reductase activity of products of the genes. In some embodiments, the *E. coli* comprises one or both wild type genes (or otherwise functional genes encoding enzymes) selected from the group consisting of ilvE and poxB genes. Specifically, the present disclosure includes recombinant *E. coli* containing mutations in four, five or six endogenous ADH genes, including adhE, yqhD, adhP, eutG, yiaY, and yjgB. In one embodiment, all six ADHs are deleted. In another embodiment, all six ADHs contain point mutations which reduce (or eliminate) alcohol dehydrogenase and/or aldehyde reductase activity of products of those genes. In some embodiments, alcohol dehydrogenase and/or aldehyde reductase activity is reduced by a combination of deletion(s) and point mutation(s). The disclosure further includes recombinant *E. coli* containing mutations in four, five or six endogenous genes with IBR activity, including adhE, yqhD, adhP, eutG, yjgB, and fucO. In one embodiment, all six IBRs are deleted. In another embodiment, all six IBRs contain point mutations which reduce (or eliminate) isobutyraldehyde reductase activity of products of those genes. In some embodiments, isobutyraldehyde reductase activity is reduced by a combination of deletion(s) and point mutation(s). In one embodiment, the recombinant *E. coli* also contain an enzyme or enzymes that catalyze the conversion from 2-keto-acids to aldehydes, which can be further converted to other non-alcohol chemicals. In one specific embodiment, the recombinant *E. coli* contain a 2-keto-acid decarboxylase (KDC) to catalyze the conversion. Exemplary KDC include Pdc, Pdc1, Pdc5, Pdc6, Aro10, Thi3, Kivd, and KdcA. In addition, the disclosure also includes recombinant *E. coli* further optimized for the production of particular aldehydes or non-alcohol chemicals. *E. coli*'s native amino acid biosynthesis pathways can be modified to produce aldehydes or non-alcohol chemicals. The 2-keto-acids are present as natural intermediates in *E. coli*'s amino acid biosynthesis pathways. In one embodiment, the recombinant *E. coli* produce increased levels of a 2-keto-acid as compared to wild type *E. coli*. n one embodiment, the recombinant *E. coli* produce increased level of 2-ketoisovalerate as compared to wild type *E. coli*. The *E. coli* may have elevated expression or activity of acetohydroxy acid synthase or acetolactate synthase, acetohydroxy acid isomeroreductase, or dihydroxy-acid dehydratase, or any combination of the foregoing, as compared to wild type *E. coli*. In one specific embodiment, the *E. coli* have elevated expression or activity of AlsS, IlvC, and IlvD as compared to wild type *E. coli*. In a further embodiment, the *E. coli* contain one or more mutations or deletions of genes fnr, ldhA, frdBC, pflB, and pta. In another embodiment, the recombinant *E. coli* produce increased level of 2-ketovalerate as compared to wild type *E. coli*. The *E. coli* may have elevated expression or activity of α-isopropylmalate synthase, β-isopropylmalate dehydrogenase, α-isopropylmalate isomerase or threonine dehydratase, or any combination of the foregoing, as compared to wild type

*E. coli*. In one specific embodiment, the *E. coli* have elevated expression or activity of LeuA, LeuCD, LeuB, or IlvA, or any combination of the foregoing, as compared to wild type *E. coli*. In yet another embodiment, the recombinant *E. coli* produce increased level of 2-keto-3-methyl-valerate as compared to wild type *E. coli*. The *E. coli* may have elevated expression or activity of threonine dehydratase, acetohydroxy acid synthase or acetolactate synthase, acetohydroxy acid isomeroreductase or dihydroxy-acid dehydratase or any combination of the foregoing, as compared to wild type *E. coli*. In one specific embodiment, the *E. coli* have elevated expression or activity of IlvA, AlsS, IlvC, or IlvD, or any combination of the foregoing, as compared to wild type *E. coli*. In one embodiment, the recombinant *E. coli* produce increased level of 2-keto-4-methyl-pentanoate as compared to wild type *E. coli*. The *E. coli* may have elevated expression or activity of acetohydroxy acid synthase or acetolactate synthase, acetohydroxy acid isomeroreductase, dihydroxy-acid dehydratase, α-isopropylmalate synthase, α-isopropylmalate isomerase, or β-isopropylmalate dehydrogenase, or any combination of the foregoing, as compared to wild type *E. coli*. In one specific embodiment, the *E. coli* have elevated expression or activity of AlsS, IlvC, IlvD, LeuA, LeuCD, or LeuB, or any combination of the foregoing, as compared to wild type *E. coli*. In another embodiment, the recombinant *E. coli* produce increased level of 2-ketobutyrate as compared to wild type *E. coli*. The *E. coli* may have elevated expression or activity of threonine dehydratase as compared to wild type *E. coli*. In one specific embodiment, the *E. coli* have elevated expression or activity of INA as compared to wild type *E. coli*. In yet another embodiment, the recombinant *E. coli* produce increased level of phenylpyruvate as compared to wild type *E. coli*. The *E. coli* may have elevated expression or activity of chorismate mutase P/prephenate dehydratase and/or chorismate mutase T/prephenate dehydrogenase as compared to wild type *E. coli*. In one specific embodiment, the *E. coli* have elevated expression or activity of PheA and/or TyrA as compared to wild type *E. coli*. In one aspect, the disclosure includes methods of producing *E. coli* with substantially reduced alcohol dehydrogenase and/or aldehyde reductase activity through targeted modifications of four, five or six of the adhE, yqhD, adhP, eutG, yiaY, and yjgB genes. In another aspect, the disclosure includes methods of producing *E. coli* with substantially reduced isobutyraldehyde reductase activity through targeted modifications of four, five or six of the adhE, yqhD, adhP, eutG, yjgB, and fucO genes.

In another aspect, the disclosure includes methods for improving production of higher aldehydes, or non-alcohol chemicals further derived from the higher aldehydes. In some embodiments, the aldehyde is isobutyraldehyde, butyraldehyde, 2-methyl-butyraldehyde, 3-methyl-butyraldehyde, propionaldehyde, or phenylacetaldehyde. The methods include providing recombinant *E. coli* as described in the preceeding paragraph, culturing the *E. coli* in the presence of a suitable substrate or metabolic intermediate and under conditions suitable for the conversion of the substrate to an aldehyde or a non-alcohol chemical derived from the aldehyde, and substantially purifying the aldehyde or the non-alcohol chemical. In one embodiment, a method for producing isobutyraldehyde is provided. The method includes providing recombinant *E. coli* which contain substantially reduced alcohol-dehydrogenase and/or isobutyraldehyde reductase activity and overexpression of a 2-keto-acid decarboxylase. The *E. coli* can further contain increased level of 2-ketoisovalerate as compared to wild type *E. coli*. The method further includes the step of culturing the *E. coli* in the presence of a suitable substrate or metabolic intermediate and under conditions suitable for the conversion of the substrate to isobutyraldehyde, and substantially purifying the isobutyraldehyde. In another embodiment, a method for producing butyraldehyde is provided. The method includes providing recombinant *E. coli* which contain substantially reduced alcohol-dehydrogenase activity and overexpression of a 2-keto-acid decarboxylase. The *E. coli* can further contain increased level of 2-ketovalerate as compared to wild type *E. coli*. The method further includes the steps of culturing the *E. coli* in the presence of a suitable substrate or metabolic intermediate and under conditions suitable for the conversion of the substrate to butyraldehyde, and substantially purifying the butyraldehyde. In yet another embodiment, a method for producing 2-methyl-butyraldehyde is provided. The method includes providing recombinant *E. coli* which contain substantially reduced alcohol dehydrogenase and/or aldehyde reductase activity and overexpression of a 2-keto-acid decarboxylase. The *E. coli* can further contain increased level of 2-keto-3-methyl-valerate as compared to wild type *E. coli*. The method further includes the step of culturing the *E. coli* in the presence of a suitable substrate or metabolic intermediate and under conditions suitable for the conversion of the substrate to 2-methyl-butyraldehyde, and substantially purifying the 2-methyl-butyraldehyde. In one embodiment, a method for producing 3-methyl-butyraldehyde is provided. The method includes providing recombinant *E. coli* which contain substantially reduced alcohol dehydrogenase and/or aldehyde reductase activity and overexpression of a 2-keto-acid decarboxylase. The *E. coli* can further contain increased level of 2-keto-4-methyl-pentanoate as compared to wild type *E. coli*. The method further includes the step of culturing the *E. coli* in the presence of a suitable substrate or metabolic intermediate and under conditions suitable for the conversion of the substrate to 3-methyl-butyraldehyde, and substantially purifying the 3-methyl-butyraldehyde. In another embodiment, a method for producing propionaldehyde is provided. The method includes providing recombinant *E. coli* which contain substantially reduced alcohol dehydrogenase and/or aldehyde reductase activity and overexpression of a 2-keto-acid decarboxylase. The *E. coli* can further contain increased level of propionaldehyde as compared to wild type *E. coli*. The method further includes the step of culturing the *E. coli* in the presence of a suitable substrate or metabolic intermediate and under conditions suitable for the conversion of the substrate to propionaldehyde, and substantially purifying the propionaldehyde. In yet another embodiment, a method for producing phenylacetaldehyde is provided. The method includes providing recombinant *E. coli* which contain substantially reduced alcohol dehydrogenase and/or aldehyde reductase activity and overexpression of a 2-keto-acid decarboxylase. The *E. coli* can further contain increased level of phenylpyruvate as compared to wild type *E. coli*. The method further includes the step of culturing the *E. coli* in the presence of a suitable substrate or metabolic intermediate and under conditions suitable for the conversion of the substrate to a phenylacetaldehyde, and substantially purifying the phenylacetaldehyde. In one specific embodiment, the suitable substrate described above is glucose. Additionally, the disclosure includes methods of purifying higher aldehydes or other non-alcohol chemicals. In some embodiments, the methods for purifying the isobutyraldehyde, butyraldehyde, or propionaldehyde include the steps of removing the aldehydes from the culture medium during production by the bubbling of air, and condensing the evaporated aldehydes. In some specific embodiments, the isobutyraldehyde, butyraldehyde, or propionaldehyde is condensed with a Graham condenser.

The present disclosure also provides a bacterium comprising a mutation in each of yahK, ybbO, gldA, dkgA/yqhE, and yghA genes, wherein the mutation reduces isobutyraldehyde reductase activity of products of the genes. In some embodiments, the bacterium comprises a further mutation in an eutE gene, wherein the further mutation reduces aldehyde dehydrogenase reductase activity of a product of the eutE gene. In some embodiments, the bacterium comprises a still further mutation in each of adhE, yqhD, adhP, and eutG genes, wherein the mutation reduces alcohol dehydrogenase activity and/or isobutyraldehyde reductase activity of products of the genes. In some preferred embodiments, the bacterium comprises a mutation in each of adhE, yqhD, adhP, eutG, and yjgB genes. In a subset of these embodiments, the bacterium comprises one or both wild type genes (or otherwise functional genes encoding enzymes) selected from the group consisting of ilvE and poxB genes. In some embodiments, the bacterium comprises a mutation in each of adhE, yqhD, adhP, eutG, yiaY, and yjgB genes, wherein the mutation reduces alcohol dehydrogenase activity of products of the genes. In some preferred embodiments, the bacterium comprises a mutation in each of adhE, yqhD, adhP, eutG, fucO, and yjgB genes, wherein the mutation reduces isobutyraldehyde reductase activity of products of the genes. In some preferred embodiments, the bacterium comprises a mutation in each of adhE, yqhD, adhP, eutG, yiaY, yjgB, betA, and fucO genes. In some particularly preferred embodiment, the bacterium is E. coli. In some embodiments, the bacterium further comprises a 2-keto-acid decarboxylase, and the bacterium produces an increased level of a 2-keto-acid as compared to a comparable wild type bacterium (e.g., same genus and species as the claimed bacterium lacking the mutations). In some embodiments, the 2 keto-acid is 2-ketoisovalerate. In some preferred embodiments, the 2-keto-acid decarboxylase is Kivd, or a homolog having 2-keto-acid decarboxylase activity and having at least 60% sequence identity to Kivd. In some embodiments, Kivd encoded by kivd of L. lactis. In some embodiments, the bacterium has elevated expression or activity of: a) acetohydroxy acid synthase or acetolactate synthase; b) acetohydroxy acid isomeroreductase; or c) dihydroxy-acid dehydratase; or any combination of the foregoing, as compared to a comparable wild type bacterium. In some preferred embodiments, the bacterium has elevated expression or activity of AlsS, IlvC, and IlvD as compared to a comparable wild type bacterium. In some embodiments, AlsS encoded by alsS of B. subtilis; IlvC encoded by ilvC of E. coli; and IlvD encoded by ilvD of E. coli. In some embodiments, the bacterium further comprises a deletion of fnr, ldhA, frdBC, pflB, and pta genes. In some embodiments, the bacterium contains one or more (e.g., one, two, three, . . . 37, 38 or 39) wild-type genes (or otherwise functional genes encoding enzymes) selected from the group consisting of: yphC, ycjQ, ybdR, rspB, ydjG, ghrB, yjjN, ydfG, dkgB, ydjJ, ydjL, yhdH, yeaE, yghZ, TAS, ygbJ, ghrA, ycjS, yceM, yhiN, yhhX, ydbC, ygjR, ygfF, yohF, yciK, ykgE, ygcW, upcA, yajO, hdhA, ydhF, ybiC, TDH, yggP, yqiB, frmA, yjhC, ydgJ, and ykgE genes. Additionally the present disclosure provides methods for producing an aldehyde, comprising: (a) providing the bacterium; (b) culturing the bacterium of (a) in culture medium comprising a suitable substrate or metabolic intermediate under conditions suitable for the conversion of the substrate or intermediate to an aldehyde; and (c) substantially purifying the aldehyde. In some preferred embodiments, the step of purifying the aldehyde comprises: (i) bubbling air while culturing the bacterium to evaporate the aldehyde from the culture medium; and (ii) condensing the evaporated aldehyde. In some embodiments, the step of condensing is done with a Graham condenser. In some preferred embodiments, the aldehyde is isobutyraldehyde, butyraldehyde, or propionaldehyde.

Furthermore the present disclosure provides an E. coli comprising a mutation in each of adhE, yqhD, adhP, and eutG genes, wherein the mutation reduces alcohol dehydrogenase activity and/or isobutyraldehyde reductase activity of products of the genes. In some embodiments, the E. coli comprises a mutation in each of adhE, yqhD, adhP, eutG, and yjgB genes. In some embodiments, the E. coli comprises one or both wild type genes (or otherwise functional genes encoding enzymes) selected from the group consisting of ilvE and poxB genes. In some preferred embodiments, the E. coli comprises a mutation in each of adhE, yqhD, adhP, eutG, yiaY, and yjgB genes, wherein the mutation reduces alcohol dehydrogenase activity of products of the genes. In some preferred embodiments, the E. coli comprises a mutation in each of adhE, yqhD, adhP, eutG, fucO, and yjgB genes, wherein the mutation reduces isobutyraldehyde reductase activity of products of the genes. In some embodiments, the E. coli comprises a mutation in each of adhE, yqhD, adhP, eutG, yiaY, yjgB, betA, and fucO genes. In some particularly preferred embodiments, the E. coli further comprises a 2-keto-acid decarboxylase, and the E. coli produces an increased level of a 2-keto-acid as compared to wild type E. coli. In some embodiments, the 2 keto-acid is 2-ketoisovalerate. In some embodiments, the 2-keto-acid decarboxylase is Kivd, or a homolog having 2-keto-acid decarboxylase activity and having at least 60% sequence identity to Kivd. In some embodiments, Kivd encoded by kivd of L. lactis. In some embodiments, the E. coli has elevated expression or activity of: a) acetohydroxy acid synthase or acetolactate synthase; b) acetohydroxy acid isomeroreductase; c) dihydroxy-acid dehydratase; or any combination of the foregoing, as compared to wild type E. coli. In some embodiments, the E. coli has elevated expression or activity of AlsS, IlvC, and IlvD as compared to wild type E. coli. In some embodiments, AlsS encoded by alsS of B. subtilis; IlvC encoded by ilvC of E. coli; and IlvD encoded by ilvD of E. coli. In some embodiments, the E. coli further comprises a deletion of fnr, ldhA, frdBC, NW, and pta genes. Additionally the present disclosure provides methods for producing an aldehyde, comprising: (a) providing the E. coli; (b) culturing the E. coli of (a) in culture medium comprising a suitable substrate or metabolic intermediate under conditions suitable for the conversion of the substrate or intermediate to an aldehyde; and (c) substantially purifying the aldehyde. In some embodiments, the step of purifying the aldehyde comprises: (i) bubbling air while culturing the E. coli to evaporate the aldehyde from the culture medium; and (ii) condensing the evaporated aldehyde. In some embodiments, the step of condensing is done with a Graham condenser. In some embodiments, the aldehyde is isobutyraldehyde, butyraldehyde, or propionaldehyde.

Moreover the present disclosure provides an E. coli of the preceeding paragraph comprising a further mutation in each of yahK, ybbO, gldA, dkgA/yqhE, and yghA genes, wherein the further mutation reduces isobutyraldehyde reductase activity of products of the genes. In some embodiments, the E. coli comprises a still further mutation in an eutE gene, wherein the still further mutation reduces aldehyde dehydrogenase reductase activity of a product of the eutE gene. In some particularly preferred embodiments, the *E. coli* further comprises a 2-keto-acid decarboxylase, and the *E. coli* produces an increased level of a 2-keto-acid as compared to wild type *E. coli*. In some preferred embodiments, the *E. coli* comprises elevated expression and/or activity of: a) 2-keto-acid decarboxylase; b) acetohydroxy acid synthase or acetolactate synthase; c) acetohydroxy acid isomeroreductase; d) dihydroxy-acid dehydratase; or any combination of the foregoing, as compared to wild type *E. coli*. In some embodiments, the *E. coli* has elevated expression or activity of Kivd, AlsS, IlvC, and IlvD as compared to wild type *E. coli*. In some embodiments, Kivd is encoded by kivd of *L. lactis*, AlsS is encoded by alsS of *B. subtilis*; IlvC is encoded by ilvC of *E. coli*; and IlvD is encoded by ilvD of *E. coli*. In some embodiments, the *E. coli* further comprises a deletion of fnr, ldhA, frdBC, NW, and pta genes. n some embodiments, the *E. coli* contains one or more (e.g., one, two, three, . . . 37, 38 or 39) wild-type genes (or otherwise functional genes encoding enzymes) selected from the group consisting of: yphC, ycjQ, ybdR, rspB, ydjG, ghrB, yjjN, ydfG, dkgB, ydjJ, ydjL, yhdH, yeaE, yghZ, TAS, ygbJ, ghrA, ycjS, yceM, yhiN, yhhX, ydbC, ygjR, ygfF, yohF, yciK, ykgE, ygcW, upcA, yajO, hdhA, ydhF, ybiC, TDH, yggP, yqiB, frmA, yjhC, ydgJ, and ykgE genes. Additionally the present disclosure provides methods for producing an aldehyde, comprising: (a) providing an *E. coli*; (b) culturing the *E. coli* of (a) in culture medium comprising a suitable substrate or metabolic intermediate under conditions suitable for the conversion of the substrate or intermediate to an aldehyde; and (c) substantially purifying the aldehyde. In some embodiments, the step of purifying the aldehyde comprises: (i) bubbling air while culturing the *E. coli* to evaporate the aldehyde from the culture medium; and (ii) condensing the evaporated aldehyde. In some embodiments, the step of condensing is done with a Graham condenser. In some embodiments, the aldehyde is isobutyraldehyde, butyraldehyde, or propionaldehyde. Also provided are methods for producing the *E. coli*, comprising: introducing a mutation in each of the genes, wherein the mutation reduces alcohol dehydrogenase activity and/or isobutyraldehyde reductase activity of products of the genes.

BRIEF DESCRIPTION OF THE DRAWINGS

FIG. 11A shows that AL626 and AL1448 are able to produce similar amounts of isobutyraldehyde. FIG. 11 B shows that AL1448 produces about 60% less isobutanol as compared to AL626. Note that FIG. 11B depicts the same isobutanol data as FIG. 11A but on a smaller y-axis scale.

DETAILED DESCRIPTION OF THE INVENTION

Figure 1:
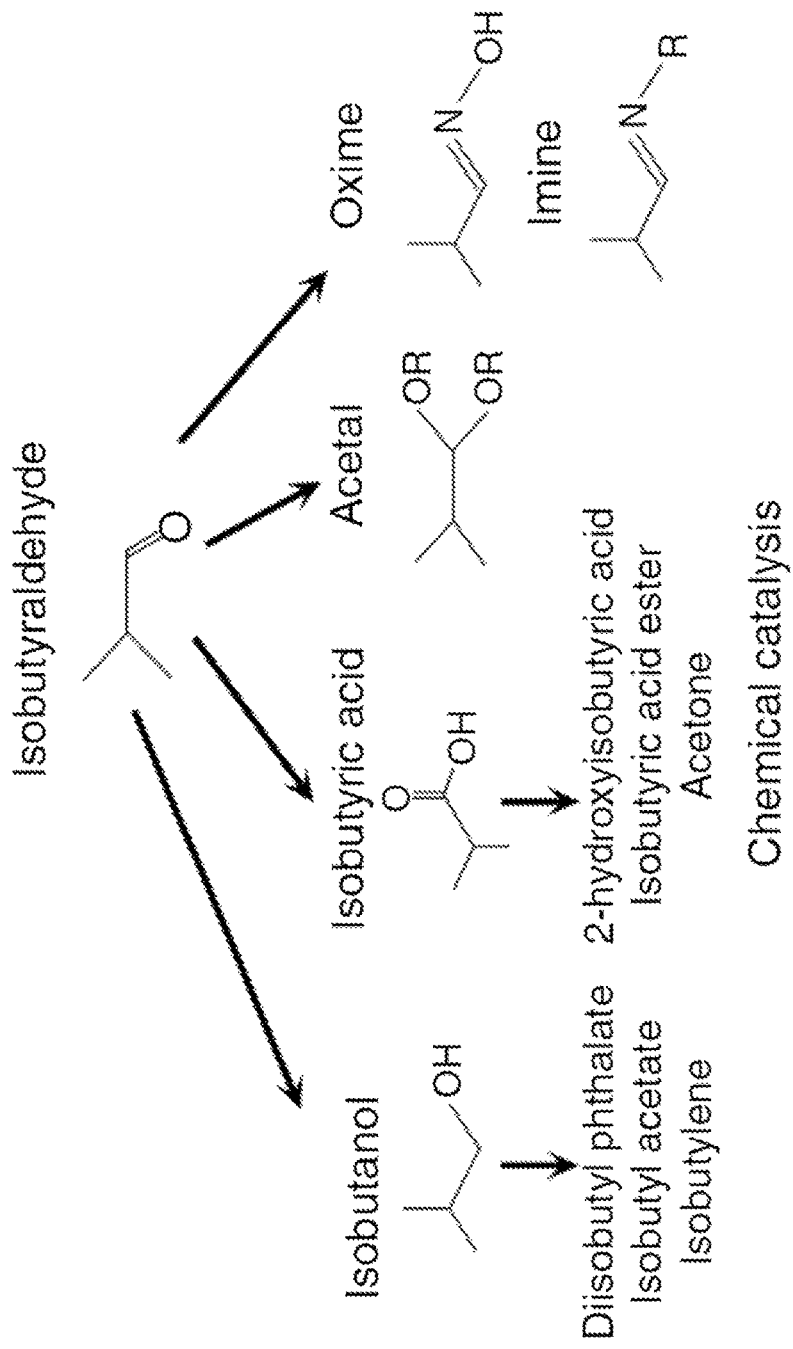
FIG. 1 illustrates how isobutyraldehyde is a precursor for the synthesis of other industrially useful chemicals.

The present disclosure relates to recombinant *E. coli* and other bacteria with substantially reduced alcohol dehydrogenase and/or aldehyde reductase activity and to methods of using these *E. coli* and other bacteria to produce non-alcohol chemicals from suitable carbon sources. The present disclosure further relates to recombinant *E. coli* and other bacteria with substantially reduced isobutyraldehyde reductase activity for the production of non-alcohol chemicals from suitable carbon sources.

E. coli with Substantially Reduced Alcohol Dehydrogenase and/or Isobutyraldehyde Reductase Activities E. coli have six different alcohol dehydrogenases (ADHs), adhE, yqhD, adhP, eutG, yiaY, and yjgB, which together contribute to most of the endogenous alcohol dehydrogenase activity. Studies described herein reveal the surprising finding that these genes share a high degree of redundancy and multiple mutations are required to obtain a strain with substantially reduced alcohol dehydrogenase and/or aldehyde reductase activity. The recombinant E. coli of this invention contain targeted genetic modifications in at least four of the six endogenous ADH genes and have substantially less alcohol dehydrogenase and/or aldehyde reductase activity as compared to wild type E. coli.

E. coli have six different isobutyraldehyde reductases (IBRs), adhE, yqhD, adhP, eutG, yjgB, and fucO, which together contribute to most of the endogenous isobutyraldehyde reductase activity. The recombinant E. coli of this invention contain targeted genetic modifications in at least four of the six endogenous IBR genes and have substantially less isobutyraldehyde reductase activity as compared to wild type E. coli.

Additionally, E. coli have five enzymes (encoded by yahK, ybbO, gldA, dkgA/yqhE, and yghA) that also possess isobutyraldehyde reductase activity. The recombinant E. coli of this invention contain targeted genetic modifications in four or more of the endogenous ADH/IBR genes (e.g., adhE, yqhD, adhP, and eutG genes) as well as all one, two, three, four or five of the group consisting of yahK, ybbO, gldA, dkgA/yqhE, and yghA, and have substantially less isobutyraldehyde reductase activity as compared to wild type E. coli. In some embodiments, the E. coli comprises one or both wild type (or otherwise functional genes) selected from the group consisting of ilvE (e.g., EcoCyc Accession No. EG10497) and poxB (e.g., EcoCyc Accession No. EG10754) genes.

In one embodiment the recombinant E. coli strains contain mutations in four of the six ADH genes, including adhE, yqhD and two of the other four ADHs, adhP, eutG, yiaY, and yjgB, and the mutations together substantially reduce or eliminate the endogenous alcohol dehydrogenase and/or aldehyde reductase activity of the cell.

In one embodiment the recombinant E. coli strains contain mutations in four of the six IBR genes, including adhE, yqhD and two of the other four ADHs, adhP, eutG, fucO, and yjgB, and the mutations together substantially reduce or eliminate the endogenous isobutyraldehyde reductase activity of the cell.

In another embodiment the recombinant E. coli strains contain mutations in five of the six ADH genes, including adhE, yqhD and three of the other four ADHs, adhP, eutG, yiaY, and yjgB, and the mutations together substantially reduce or eliminate the endogenous alcohol dehydrogenase and/or aldehyde reductase activity of the cell.

In another embodiment the recombinant E. coli strains contain mutations in five of the six IBR genes, including adhE, yqhD and three of the other four ADHs, adhP, eutG, fucO, and yjgB, and the mutations together substantially reduce or eliminate the endogenous isobutyraldehyde reductase activity of the cell.

In yet another embodiment the recombinant E. coli strains contain mutations in all the six ADH genes, adhE, yqhD, adhP, eutG, yiaY, and yjgB, and the mutations together substantially reduce or eliminate the endogenous alcohol dehydrogenase and/or aldehyde reductase activity of the cell.

In yet another embodiment the recombinant E. coli strains contain mutations in all six IBR genes, adhE, yqhD, adhP, eutG, fucO, and yjgB, and the mutations together substantially reduce or eliminate the endogenous isobutyraldehyde reductase activity of the cell.

In yet another embodiment the recombinant E. coli strains contain mutations in all six IBR genes, adhE, yqhD, adhP, eutG, fucO, and yjgB, plus yahK, ybbO, gldA, dkgA/yqhE, and yghA, and the mutations together even more substantially reduce endogenous isobutyraldehyde reductase activity of the cell.

The mutations of the enzymes decrease the activity of enzymes by 70%, 75%, 80%, 85%, 90%, 95%, 98%, 99% or 100% relative to wild type enzymes. Mutations that reduce or eliminate the activity of enzymes may include point mutations that cause amino acid changes in the enzymes, deletion mutations, nonsense mutations, frameshift mutations, sequence duplications or inversions and insertions. Mutations can be introduced by molecular biology means, such as homologous recombinations, antisense technologies or RNA interference, or by chemical means, such as treatments with DNA intercalators or DNA methylating agents followed by a secondary screening step wherein the strains are selected for substantially reduced alcohol dehydrogenase and/or aldehyde reductase activity.

In one specific embodiment, the E. coli strains contain deletions of all six ADHs, adhE, yqhD, adhP, eutG, yiaY, and yjgB. In another specific embodiment, the E. coli strains contain point mutations in all six ADHs that reduce or eliminate their alcohol dehydrogenase and/or aldehyde reductase activity. ADHs are known to be well conserved among species (Jornvall et al., Eur. J. Biochem. 1987: 167, 195-20). Previous studies have identified amino acid residues in mammalian ADHs that are critical for their alcohol dehydrogenase activity. (See Biochemistry. 1990 Feb. 6; 29(5):1112-8; J Biol Chem. 1990 Sep. 25; 265(27):16366-72; J Biol Chem. 1992 Mar. 15; 267(8):5527-33; FEBS Lett. 1993 Mar. 15; 319(1-2):90-4.) Those of skill in the art can predict which amino acid residues of E. coli ADHs are critical to their alcohol dehydrogenase and/or aldehyde reductase activity using homology searches and generate E. coli strains containing point mutations in all six ADHs that reduce or eliminate their alcohol dehydrogenase and/or aldehyde reductase activity.

In one specific embodiment, the E. coli strains contain deletions of all six IBRs, adhE, yqhD, adhP, eutG, fucO, and yjgB. In another specific embodiment, the E. coli strains contain point mutations in all six IBRs that reduce or eliminate their isobutyraldehyde reductase activity. Those of skill in the art can predict which amino acid residues of E. coli IBRs are critical to their isobutyraldehyde reductase activity using homology searches and generate E. coli strains containing point mutations in all six IBRs that reduce or eliminate their isobutyraldehyde reductase activity.

In some specific embodiments, the E. coli strains contain mutations in all six IBRs, as well as yahK, ybbO, gldA, dkgA/yqhE, and yghA genes, that reduce or eliminate their isobutyraldehyde reductase activity.

Enzymatic reactions can be classified according to their Enzyme Commission (EC) number. The EC number associated with a given enzyme specifies the classification of the type of enzymatic reaction that a given enzyme is capable of catalyzing. EC numbers do not specify identities of enzymes, but instead specify the identity of the chemical reaction that a given enzyme catalyzes. Similarly, proteins can also be assigned Gene Ontology (GO) terms. GO terms attempt to further define the given role and/or function of a protein in a living organism by specifying protein function in terms of a cellular component, a biological process, and/or a molecular function. For example, two enzymes from two different species of organisms that catalyze the same chemical reaction could be assigned the same EC classification and GO term annotation, despite that the respective enzymes are endogenous to different organisms. EC and GO term classifications are helpful to those skilled in the art in identifying the molecular function and/or activity of a given protein outside of knowing its unique identifying classification with regard to the organism it came from, such as its NCBI (National Council for Biotechnology) identifier. EC and GO term classifications may encompass broad or very narrow enzymatic activities and functions, and many proteins are classified under several often overlapping EC and GO terms. The classifications listed in this disclosure are included to describe enzymes and genes that could be utilized in certain embodiments. They are provided to help those skilled in the art understand the enzymatic activity or class of interest and are not meant to limit or restrict choice of enzymes in the embodiments.

ADH and IBR gene products may be identified as having EC classification 1.1.1.1 and/or GO term ID GO: 0004022. It is important to note that EC classifications only describe the capability of an enzyme to catalyze a reaction; they do not predict the function of an enzyme under particular circumstances. As the examples of the current disclosure show, functional testing must be carried out to determine which enzymes with a certain EC classification are capable of catalyzing certain reactions under a given set of conditions.

E. coli with Further Reduced Isobutyraldehyde Reductase Activity

As shown in the present disclosure, E. coli have six different isobutyraldehyde reductases (IBRs), adhE, yqhD, adhP, eutG, yjgB, and fucO, which contribute to most of the endogenous isobutyraldehyde reductase activity. Furthermore, E. coli have six different alcohol dehydrogenases (ADHs), adhE, yqhD, adhP, eutG, yiaY, and yjgB, which contribute to most of the endogenous alcohol dehydrogenase activity. E. coli lacking adhE, yqhD, adhP, eutG, yiaY, yjgB, betA, and fucO have substantially reduced aldehyde reductase (ALR) activity as compared to wild type E. coli. It is therefore surprising that when E. coli lacking these eight genes produce isobutyraldehyde for longer than 2 days, they begin to generate significant amounts of isobutanol as well. This unexpected result indicates that still further enzymes act as ALR under these conditions. As described in Example 3, yahK, ybbO, gldA, dkgA (yqhE), and yghA each encode enzymes that possess ALR activity. When mutated in combination, their loss results in a reduction in E. coli ALR activity and in the production of isobutanol compared to E. coli wherein these genes are functional.

E. coli for Producing Aldehydes or Non-Alcohol Chemicals Derived from Aldehydes

A. Recombinant E. coli that Convert 2-Keto-Acids to Higher Aldehydes

In one embodiment, recombinant E. coli that produce higher aldehydes or non-alcohol chemicals derived from aldehydes are provided. The aldehydes which are produced include isobutyraldehyde, butyraldehyde, 2-methyl-butyraldehyde, 3-methyl-butyraldehyde, propionaldehyde, or phenylacetaldehyde. 2-keto-acids are natural intermediates in the amino acid biosynthesis pathways of E. coli. In certain embodiments, the recombinant E. coli of the invention contain 2-keto-acid decarboxylase (KDC). In other embodiments, the recombinant E. coli contain multiple enzymes which together catalyze conversion of 2-keto-acids to aldehydes via multiple intermediates instead of a single enzyme which directly catalyzes conversion of 2-keto-acids to aldehydes.

The 2-keto-acids present as natural intermediates in the amino acid biosynthesis pathway in E. coli include 2-ketoisovalerate, 2-ketovalerate, 2-keto-3-methylvalerate, 2-keto-4-methyl-pentanoate, 2-ketobutyrate, and phenylpyruvate. Accordingly, in certain embodiments, the recombinant E. coli that produce aldehydes or non-alcohol chemicals derived from aldehydes contain an enzyme or multiple enzymes that catalyze the conversion from 2-ketoisovalerate to isobutyraldehyde, from 2-ketovalerate to butyraldehyde, from 2-keto-3-methyl-valerate to 2-methyl-butyraldehyde, from 2-keto-4-methyl-pentanoate to 3-methyl-butyraldehyde, from 2-ketobutyrate to propionaldehyde, or from phenylpyruvate to phenylacetaldehyde.

In a preferred embodiment, the enzyme which converts the 2-keto-acids to aldehydes is 2-keto-acid decarboxylase. The 2-keto-acid decarboxylase can be derived from bacterial or yeast source. 2-keto-acid decarboxylase enzymes catalyze the enzymatic reaction belonging to the classifications EC 4.1.1.1, EC 4.1.1.72, or EC 4.1.1.74. They share the molecular function of GO term IDs GO: 0016831 (decarboxylase activity) and/or GO: 0004737 (2-keto-acid decarboxylase activity). Any protein characterized with these EC classifications and/or GO terms may possess catalytic 2-keto-acid decarboxylase activity. Exemplary KDCs include Pdc, Pdcl, Pdc5, Pdc6, Aro10, Thi3, Kivd, and KdcA. In some embodiments, the recombinant E. coli contain a homolog or variant of the aforementioned KDCs, or a polypeptide having at least 60% identity to any one of the foregoing and having 2-keto-acid decarboxylase activity. In a specific embodiment, the 2-keto-acid decarboxylase is encoded by a polynucleotide derived from a kivd gene from *Lactococcus lactis*, or homolog thereof. In other embodiments, the KDC is Pdc6 from *Saccharomyces cerevisiae*, Aro10 from *Saccharomyces cerevisiae*, Thi3 from *Saccharomyces cerevisiae* or Pdc from *Clostridium acetobutylicum*, or homologs thereof. Other KDCs known in the art include but are not limited to gi|428770248|ref|YP_007162038.1| Pyruvate decarboxylase [*Cyanobacterium aponinum* PCC 10605]; gi|470462934|ref|YP_007629245.1| Pyruvate decarboxylase; Alpha-keto-acid decarboxylase [*Edwardsiella tarda* C07-087]; gi|325106918|ref|YP_004267986.1| pyruvate decarboxylase [*Planctomyces brasiliensis* DSM 5305]; gi|20385191|gb|AAM21208.1|AF368435_1 pyruvate decarboxylase [*Acetobacter pasteurianus*]; gi|506381688|ref|WP_015901407.1| pyruvate decarboxylase [*Staphylococcus carnosus*]; gi|475988405|gb|EMU49652.1| pyruvate decarboxylase [*Acinetobacter baumannii* ABNIH24]; gi|167374781|gb|ABZ79223.1| pyruvate decarboxylase [*Prunus armeniaca*]; gi|453062165|gb|EMF03157.1| Pyruvate decarboxylase [*Serratia marcescens* VGH107]; gi|496457580|ref|WP_009166425.1| Pyruvate decarboxylase [*Lactobacillus forum*]; gi|493981100|ref|WP_006924020.1| Pyruvate decarboxylase; Alpha-keto-acid decarboxylase [*Bacillus* sp. GeD10].

In addition to aldehydes, the recombinant E. coli provided herein can also be used to produce other non-alcohol chemicals that are further derived from aldehydes. For example, isobutyraldehyde can be further converted to isobutanol, isobutyric acid, acetal, oxime and imine (FIG. 1). In recombinant *E. coli* with substantially reduced alcohol dehydrogenase and/or aldehyde reductase activity, the conversion from isobutyraldehyde to isobutanol is substantially eliminated, increasing the flux of isobutyraldehyde into other downstream pathways for the production of non-alcohol derivatives. In one embodiment, the recombinant *E. coli* further contain elevated expression of an aldehyde dehydrogenase to facilitate the conversion from aldehyde to carboxylic acids. In one specific embodiment, the aldehyde dehydrogenase is *E. coli* γ-aminobutyraldehyde dehydrogenase YdcW. (J. Mol. Biol. 2004; 343, 29-41). Aminobutyraldehyde dehydrogenase enzymes catalyze the enzymatic reaction belonging to the classification EC 1.2.1.19. They share the molecular function of gene ontology (GO) term ID GO: 0019145. The GO term ID specifies that any protein characterized as having this associated GO term encodes an enzyme with catalytic aminobutyraldehyde dehydrogenase activity. In addition, a variety of chemical means are also available to further convert the aldehydes to other non-alcohol chemicals. (Conant, J. B. & Blatt, A. H. J. Am. Chem. Soc. 51, 1227-1236 (1929); Minne, N. & Adkins, H. J. Am. Chem. Soc. 55, 299-309 (1933); Hine, J. et al., J. Am. Chem. Soc. 92, 5186-5193 (1970). Hine, J. & Via, F. A. J. Am. Chem. Soc. 94, 190-194 (1972). Rocek, J. & Ng, C. Chromium(IV) J. Am. Chem. Soc. 96, 1522-1529 (1974)).

B. Recombinant *E. coli* Optimized for Producing Higher Aldehydes and Other Non-Alcohol Chemicals The recombinant *E. coli* described above can be optimized for production of higher aldehydes and other non-alcohol chemicals further derived from the aldehydes by genetically modifying the *E. coli* to produce increased levels of certain 2-keto-acids as compared to wild type *E. coli*.

Preferably, the recombinant *E. coli* are modified by up-regulating the native amino acid synthesis pathway. Utilizing the *E. coli*'s native amino acid synthesis pathways for production of organic chemicals offers several advantages. Not only does it avoid the difficulty of expressing a large set of foreign genes but it also minimizes the possible accumulation of toxic intermediates. The engineered amino acid biosynthetic routes for production of organic chemicals circumvent the need to involve oxygen-sensitive enzymes and CoA-dependent intermediates.

To up-regulate amino acid synthesis pathways, the recombinant *E. coli* can contain extra copies of endogenous genes encoding metabolic enzymes that contribute to the production of certain amino acids. In one embodiment, the enzymes are derived from other bacterial or yeast sources. In another embodiment, the polynucleotides engineered into the recombinant *E. coli* contain additional elements for the expression and/or regulation of expression of these genes, e.g. promoter sequences. In yet another embodiment, metabolic pathways that compete with an intermediate leading to a desired pathway can be reduced, disrupted, or knocked out. In further embodiments, certain amino acid biosynthesis pathways in *E. coli* are optimized by regulation of transcription, translation, protein stability and protein functionality using genetic engineering and appropriate culture condition.

Figure 2:
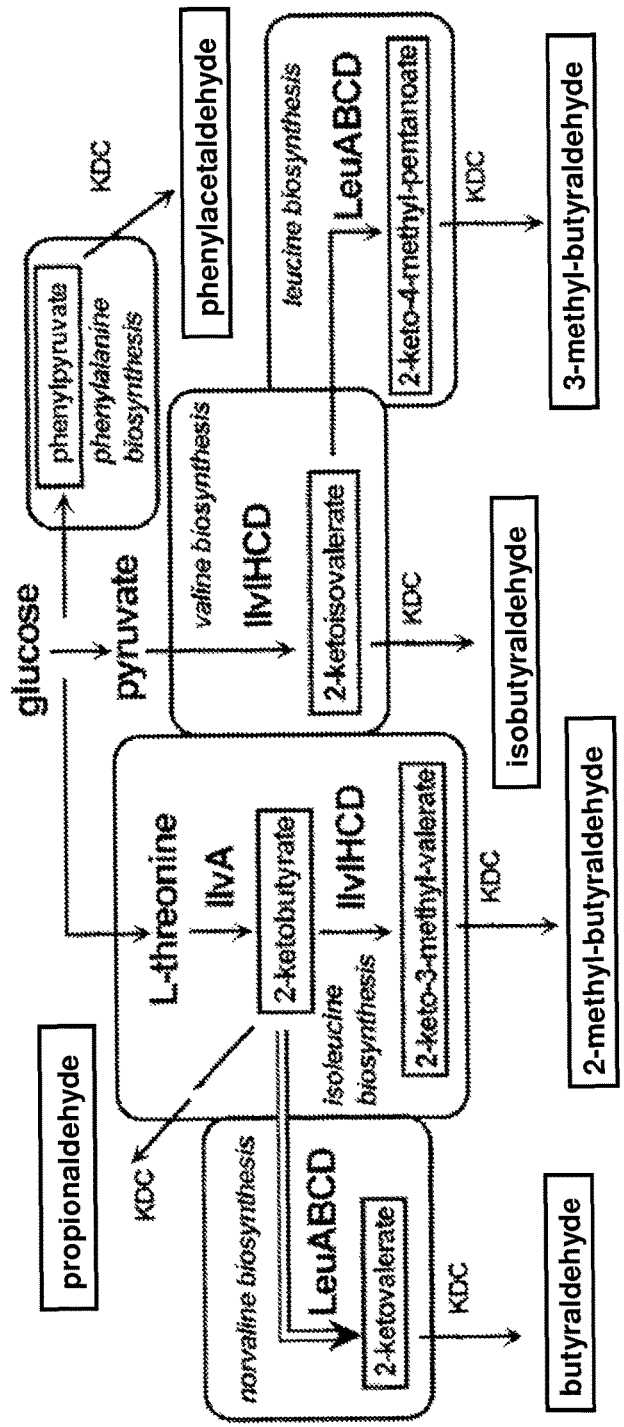
FIG. 2 illustrates the production of higher aldehydes using the endogenous amino acid biosynthesis pathways in *E. coli*.

The threonine biosynthesis pathway in *E. coli* can be utilized to enhance production of butyraldehyde, 2-methyl-butyraldehyde, propionaldehyde, and other non-alcohol chemicals derived thereof. (See FIG. 2) To increase the activity of threonine biosynthesis pathway, the recombinant *E. coli* can be engineered to have elevated expression or activity of phosphoenolpyruvate carboxylase (EC 4.1.1.31; GO: 0008964), pyruvate carboxylase (EC 6.4.1.1; GO: 0004736), aspartate aminotransferase (EC 2.6.1.1; GO: 0004069), homoserine dehydrogenase (EC 1.1.1.3; GO: 0004412), aspartate-semialdehyde dehydrogenase (EC 1.2.1.11; GO: 0004073), homoserine kinase (EC 2.7.1.39; GO: 0004413), threonine synthase (EC 4.2.3.1; GO: 0004795), L-serine dehydratase (EC 4.3.1.17; GO: 0003941), or any combination thereof, as compared to wild type *E. coli*. Any enzymes sharing the listed EC classifications or GO term IDs possess the relevant and respective enzymatic activities. In some embodiments, the phosphoenolpyruvate carboxylase, pyruvate carboxylase, aspartate aminotransferase, homoserine dehydrogenase, aspartate-semialdehyde dehydrogenase, homoserine kinase, threonine synthase, and L-serine dehydratase, are encoded by a polynucleotide derived from the ppc, pyc, aspC, thrA, asd, thrB, thrC and sdaAB genes, respectively, or homologs thereof.

The leucine biosynthesis pathway in *E. coli* can be utilized to enhance production of butyraldehyde, 3-methyl-butyraldehyde, and other non-alcohol chemicals derived thereof. (See FIG. 2) To increase the activity of leucine biosynthesis pathway, the *E. coli* can be engineered to have elevated expression or activity of α-isopropylmalate synthase (EC 4.1.3.12; GO: 0003852) β-isopropylmalate dehydrogenase (EC 1.1.1.85; GO: 0003862), α-isopropylmalate isomerase (EC 4.2.1.33; GO: 0003861), or any combination thereof, as compared to wild type *E. coli*. Any enzymes sharing the listed EC classifications or GO term IDs possess the relevant and respective enzymatic activities. In one embodiment, the α-isopropylmalate synthase is encoded by a polynucleotide derived from a leuA gene, or homologs thereof. In another embodiment, the β-isopropylmalate dehydrogenase is encoded by a polynucleotide derived from a leuB gene, or homologs thereof. In yet another embodiment, the α-isopropylmalate isomerase is encoded by a polynucleotide derived from a leuCD operon, or homologs thereof. In general the leuC gene of the leuCD operon encodes an isopropylmalate isomerase large subunit polypeptide and the leuD gene of the leuCD operon encodes an isopropylmalate isomerase small subunit polypeptide.

The valine biosynthesis pathway and isoleucine biosynthesis pathway in *E. coli* share same metabolic enzymes and can be utilized to enhance the production of isobutyraldehyde, 2-methyl-butyraldehyde, 3-methyl-butyraldehyde, and other non-alcohol chemicals derived thereof. (See FIG. 2) To increase the activity of valine biosynthesis pathway and isoleucine biosynthesis pathway, the *E. coli* can be engineered to have elevated expression or activity of acetohydroxy acid synthase or acetolactate synthase (EC 2.2.1.6; GO: 0003984), acetohydroxy acid isomeroreductase (EC 1.1.1.86; GO: 0004455), and dihydroxy-acid dehydratase (EC 4.2.1.9; GO: 0004160). Any enzymes sharing the listed EC classifications or GO term IDs possess the relevant and respective enzymatic activities. In one embodiment, the acetohydroxy acid synthase is encoded by a polynucleotide derived from an ilvIH operon, or homologs thereof. In another embodiment, the acetolactate synthase is encoded by a polynucleotide derived from an alsS gene, or homologs thereof. In another embodiment, the acetolactate synthase is encoded by a polynucleotide derived from an ilvMG operon, or homologs thereof. In yet another embodiment, the acetolactate synthase is encoded by a polynucleotide derived from an ilvNB operon, or homologs thereof. In some embodiments, the acetohydroxy acid isomeroreductase is encoded by a polynucleotide derived from an ilvC gene, or homologs thereof. In other embodiments, the dihydroxy-acid dehydratase is encoded by a polynucleotide derived from an ilvD gene, or homologs thereof.

Pyruvate can serve as a precursor for production of isobutyraldehyde, butyraldehyde, 2-methyl-butyraldehyde, 3-methyl-butyraldehyde, propionaldehyde, and other non-alcohol chemicals derived thereof. Therefore, in some specific embodiments, the recombinant *E. coli* have elevated levels of pyruvate as compared to wild type *E. coli*. In certain embodiments, the recombinant *E. coli* further contain mutations reducing or eliminating the activity of enzymes in competing pathways that utilize pyruvate as a precursor. Gene products and pathways that utilize pyruvate are depicted on KEGG (Kyoto Encyclopedia of Genes and Genomes) pathway map 00620 (available at www.genome.jp/kegg-bin/show_pathway?map00620+C00024). In one specific embodiment, the recombinant *E. coli* further include the deletion or inhibition of expression of an fnr, ldh (e.g., ldhA), frd (e.g., frdB, frdC or frdBC), pflB, and pta gene, or any combination thereof, to increase the level of pyruvate available for the isoleucine and valine biosynthetic pathways. Multiple classes of enzymes utilize pyruvate; other genes that affect pyruvate abundance may be found under the broad GO term ID GO: 0006090 (pyruvate metabolic process).

C. Preferred Embodiments

In one preferred embodiment, recombinant *E. coli* with substantially reduced alcohol dehydrogenase and/or aldehyde reductase activity that produce isobutyraldehyde are provided. The recombinant *E. coli* contain mutations in genes adhE, yqhD, adhP, eutG, yiaY, and yjgB and have increased expression or activity of 2-keto-acid decarboxylase. In another preferred embodiment, recombinant *E. coli* with substantially reduced isobutyraldehyde reductase activity that produce isobutyraldehyde are provided. The recombinant *E. coli* contain mutations in genes adhE, yqhD, adhP, eutG, fucO, and yjgB and have increased expression or activity of 2-keto-acid decarboxylase. In another preferred embodiment, recombinant *E. coli* with even more substantially reduced isobutyraldehyde reductase activity that produce isobutyraldehyde are provided. The recombinant *E. coli* contain mutations in genes adhE, yqhD, adhP, eutG, fucO, yjgB, adhE, yqhD, adhP, eutG, fucO, yjgB eutE, yahK, ybbO, gldA, dkgA/yqhE, and yghA and have increased expression or activity of 2-keto-acid decarboxylase. In yet another preferred embodiment, recombinant *E. coli* that produce isobutyraldehyde are provided wherein the *E. coli* contain mutations in genes adhE, yqhD, adhP, eutG, fucO, yjgB, yiaY, and betA. In yet another preferred embodiment, recombinant *E. coli* that produce isobutyraldehyde are provided wherein the *E. coli* additionally contain mutations in genes eutE, yahK, ybbO, gldA, dkgA/yqhE, and yghA. In some embodiments, the 2-keto-acid decarboxylase is encoded by a polynucleotide derived from a pdc6, aro10, thi3, kivd, and/or pdc gene, or homologs thereof. In one embodiment, the recombinant *E. coli* have increased levels of 2-isoketovalerate, as compared to wild type *E. coli*. (See FIG. 2) The increased levels of 2-isoketovalerate can be due to elevated expression or activity of acetohydroxy acid synthase or acetolactate synthase, acetohydroxy acid isomeroreductase, or dihydroxy-acid dehydratase. In one embodiment, the acetohydroxy acid synthase is encoded by a polynucleotide derived from an ilvIH operon, or homologs thereof. In another embodiment, the acetolactate synthase is encoded by a polynucleotide derived from an alsS gene, or homologs thereof. In another embodiment, the acetolactate synthase is encoded by a polynucleotide derived from an ilvMG operon, or homologs thereof. In one embodiment, the acetohydroxy acid isomeroreductase is encoded by a polynucleotide derived from an ilvC gene, or homologs thereof. In yet another embodiment, the dihydroxy-acid dehydratase is encoded by a polynucleotide derived from an ilvD gene, or homologs thereof. To reduce the activity of competing pathways, in one embodiment, the recombinant *E. coli* have decreased levels of 2-ketobutyrate, 2-ketovalerate, 2-keto-3-methyl-valerate, or phenylpyruvate, or any combination thereof, as compared to wild type *E. coli*. The *E. coli* may further include the deletion or inhibition of expression of ldh (e.g., an ldhA), frd (e.g., an frdB, an frdC or an frdBC), fnr, leuA, ilvE, poxB, ilvA, NW, or pta gene, or any combination thereof, to increase the availability of pyruvate for isobutyraldehyde production or reduce the activity of competing pathways.

In another embodiment, recombinant *E. coli* with substantially reduced alcohol dehydrogenase and/or aldehyde reductase activity that produces butyraldehyde are provided. The recombinant *E. coli* contain mutations in genes adhE, yqhD, adhP, eutG, yiaY, and yjgB and have increased expression or activity of 2-keto-acid decarboxylase. In some embodiments, the recombinant *E. coli* additionally contain mutations in genes eutE, yahK, ybbO, gldA, dkgA/yqhE, and yghA and have increased expression or activity of 2-keto-acid decarboxylase. In some embodiments, the 2-keto-acid decarboxylase is encoded by a polynucleotide derived from a pdc6, aro10, thi3, kivd, and/or pdc gene, or homologs thereof. In one embodiment, the recombinant *E. coli* have increased levels of 2-ketovalerate, as compared to wild type *E. coli*. (See FIG. 2) The increased levels of 2-ketovalerate can be due to elevated expression or activity of α-isopropylmalate synthase, β-isopropylmalate dehydrogenase, α-isopropylmalate isomerase, and threonine dehydratase, as compared to wild type *E. coli*. In one embodiment, the α-isopropylmalate synthase is encoded by a polynucleotide derived from a leuA gene, or homologs thereof. In another embodiment, the β-isopropylmalate dehydrogenase is encoded by a polynucleotide derived from a leuB gene, or homologs thereof. In one embodiment, the α-isopropylmalate isomerase is encoded by a polynucleotide derived from a leuCD operon, or homologs thereof. In yet another embodiment, the threonine dehydratase is encoded by a polynucleotide derived from ilvA, or tdcB gene, or homologs thereof. In another embodiment, the recombinant *E. coli* may further have elevated activity of the threonine biosynthesis pathway. In some embodiments, the recombinant *E. coli* may contain expression or activity of phosphoenolpyruvate carboxylase, pyruvate carboxylase, aspartate aminotransferase, homoserine dehydrogenase, aspartate-semialdehyde dehydrogenase, homoserine kinase, threonine synthase, L-serine dehydratase, or any combination thereof, as compared to wild type *E. coli*. In some specific embodiments, the phosphoenolpyruvate carboxylase, pyruvate carboxylase, aspartate aminotransferase, homoserine dehydrogenase, aspartate-semialdehyde dehydrogenase, homoserine kinase, threonine synthase, and L-serine dehydratase, are encoded by a polynucleotide derived from the ppc, pyc, aspC, thrA, asd, thrB, thrC and sdaAB genes, respectively, or homologs thereof. To reduce the activity of competing pathways, in another embodiment, the recombinant *E. coli* have decreased levels of 2-ketoisovalerate, 2-keto-3-methyl-valerate, 2-keto-4-methyl-pentanoate, or phenylpyruvate, or any combination thereof, as compared to wild type *E. coli*. Accordingly, the recombinant *E. coli* may further include the deletion or inhibition of expression of an ilvD gene, as compared to wild type *E. coli*. The *E. coli* may further include the deletion or inhibition of expression of ldh (e.g., an ldhA), poxB, ilvB, ilvI, metA, tdh or pta gene, or any combination thereof, to reduce the activity of competing pathways.

In another embodiment, recombinant *E. coli* with substantially reduced alcohol dehydrogenase and/or aldehyde reductase activity that produce 2-methyl-butyraldehyde are provided. The recombinant *E. coli* contain mutations in genes adhE, yqhD, adhP, eutG, yiaY, and yjgB and have increased expression or activity of 2-keto-acid decarboxylase. In some embodiments, the recombinant *E. coli* additionally contain mutations in genes eutE, yahK, ybbO, gldA, dkgA/yqhE, and yghA and have increased expression or activity of 2-keto-acid decarboxylase. In some embodiments, the 2-keto-acid decarboxylase is encoded by a polynucleotide derived from a pdc6, aro10, thi3, kivd, and/or pdc gene, or homologs thereof. In another embodiment, the recombinant *E. coli* have increased levels of 2-keto-3-methyl-valerate, as compared to wild type *E. coli*. (See FIG. 2) The increased levels of 2-keto-3-methyl-valerate can be due to elevated expression or activity of threonine dehydratase, acetohydroxy acid synthase, acetohydroxy acid isomeroreductase, and dihydroxy-acid dehydratase, as compared to wild type *E. coli*. In one embodiment, the threonine dehydratase is encoded by a polynucleotide derived from ilvA, or tdcB gene, or homologs thereof. In another embodiment, the acetohydroxy acid synthase is encoded by a polynucleotide derived from an ilvIH operon, or homologs thereof. In another embodiment, the acetolactate synthase is encoded by a polynucleotide derived from an alsS gene, or homologs thereof. In yet another embodiment, the acetolactate synthase is encoded by a polynucleotide derived from an ilvMG operon, or homologs thereof. In one embodiment, the acetohydroxy acid isomeroreductase is encoded by a polynucleotide derived from an ilvC gene, or homologs thereof. In another embodiment, the dihydroxy-acid dehydratase is encoded by a polynucleotide derived from an ilvD gene, or homologs thereof. In some embodiments, the recombinant *E. coli* may further have elevated activity of the threonine biosynthesis pathway. In some specific embodiments, the recombinant *E. coli* may contain elevated expression or activity of phosphoenolpyruvate carboxylase, pyruvate carboxylase, aspartate aminotransferase, homoserine dehydrogenase, aspartate-semialdehyde dehydrogenase, homoserine kinase, threonine synthase, L-serine dehydratase, or any combination thereof, as compared to wild type *E. coli*. In one embodiment, the phosphoenolpyruvate carboxylase, pyruvate carboxylase, aspartate aminotransferase, homoserine dehydrogenase, aspartate-semialdehyde dehydrogenase, homoserine kinase, threonine synthase, and L-serine dehydratase, are encoded by a polynucleotide derived from the ppc, pyc, aspC, thrA, asd, thrB, thrC and sdaAB genes, respectively, or homologs thereof. In yet another embodiment, to reduce the activity of competing pathways, the recombinant *E. coli* have decreased levels of 2-ketovalerate, 2-ketoisovalerate, or 2-keto-4-methyl-pentanoate, or any combination thereof, as compared to wild type *E. coli*. The *E. coli* may further include the deletion or inhibition of expression of ilvB, ilvI, metA, or tdh gene, or any combination thereof, to reduce the activity of competing pathways.

In one embodiment, recombinant *E. coli* with substantially reduced alcohol dehydrogenase and/or aldehyde reductase activity that produce 3-methyl-butyraldehyde are provided. The recombinant *E. coli* contain mutations in genes adhE, yqhD, adhP, eutG, yiaY, and yjgB and have increased expression or activity of 2-keto-acid decarboxylase. In some embodiments, the recombinant *E. coli* additionally contain mutations in genes eutE, yahK, ybbO, gldA, dkgA/yqhE, and yghA and have increased expression or activity of 2-keto-acid decarboxylase. In some embodiments, the 2-keto-acid decarboxylase is encoded by a polynucleotide derived from a pdc6, aro10, thi3, kivd, and/or pdc gene, or homologs thereof. In one embodiment, the recombinant *E. coli* have increased levels of 2-keto-4-methyl-pentanoate, as compared to wild type *E. coli*. (See FIG. 2) The increased levels of 2-keto-4-methyl-pentanoate can be due to elevated expression or activity of acetohydroxy acid synthase or acetolactate synthase, acetohydroxy acid isomeroreductase, dihydroxy-acid dehydratase, α-isopropylmalate synthase, α-isopropylmalate isomerase, and β-isopropylmalate dehydrogenase, as compared to wild type *E. coli*. In one embodiment, the acetohydroxy acid synthase is encoded by a polynucleotide derived from an ilvIH operon, or homologs thereof. In another embodiment, the acetolactate synthase is encoded by a polynucleotide derived from an alsS gene, or homologs thereof. In another embodiment, the acetolactate synthase is encoded by a polynucleotide derived from an ilvMG operon, or homologs thereof. In yet another embodiment, the acetolactate synthase is encoded by a polynucleotide derived from an ilvNB operon, or homologs thereof. In one embodiment, the acetohydroxy acid isomeroreductase is encoded by a polynucleotide derived from an ilvC gene, or homologs thereof. In another embodiment, the dihydroxy-acid dehydratase is encoded by a polynucleotide derived from an ilvD gene, or homologs thereof. In one embodiment, the α-isopropylmalate synthase is encoded by a polynucleotide derived from a leuA gene, or homologs thereof. In another embodiment, the β-isopropylmalate dehydrogenase is encoded by a polynucleotide derived from a leuB gene, or homologs thereof. In yet another embodiment, the α-isopropylmalate isomerase is encoded by a polynucleotide derived from a leuCD operon, or homologs thereof. In some embodiments, to reduce the activity of competing pathways, the recombinant *E. coli* have decreased levels of 2-ketovalerate, 2-keto-3-methyl-valerate, or 2-ketobutyrate, or any combination thereof, as compared to wild type *E. coli*. The *E. coli* may further include the deletion or inhibition of expression of ldh (e.g., an ldhA), frd (e.g., an frdB, an frdC or an frdBC), fnr, ilvE, tyrB, NW, or pta gene, or any combination thereof, to reduce the activity of competing pathways.

In another embodiment, recombinant *E. coli* with substantially reduced alcohol dehydrogenase and/or aldehyde reductase activity that produce propionaldehyde are provided. The recombinant *E. coli* contain mutations in genes adhE, yqhD, adhP, eutG, yiaY, and yjgB and have increased expression or activity of 2-keto-acid decarboxylase. In some embodiments, the recombinant *E. coli* additionally contain mutations in genes eutE, yahK, ybbO, gldA, dkgA/yqhE, and yghA and have increased expression or activity of 2-keto-acid decarboxylase. In some embodiments, the 2-keto-acid decarboxylase is encoded by a polynucleotide derived from a pdc6, aro10, thi3, kivd, and/or pdc gene, or homologs thereof. In some embodiments, the recombinant *E. coli* have increased levels of 2-ketobutyrate, as compared to wild type *E. coli*. (See FIG. 2) The increased levels of 2-ketobutyrate can be due to elevated expression or activity of threonine dehydratase as compared to wild type *E. coli*. In one embodiment, the threonine dehydratase is encoded by a polynucleotide derived from ilvA, or tdc gene (listed as tbc in the priority document), or homologs thereof. In another embodiment, the recombinant *E. coli* may further have elevated expression or activity of phosphoenolpyruvate carboxylase, pyruvate carboxylase, aspartate aminotransferase, homoserine dehydrogenase, aspartate-semialdehyde dehydrogenase, homoserine kinase, threonine synthase, L-serine dehydratase, or any combination thereof, as compared to wild type *E. coli*. In one specific embodiment, the phosphoenolpyruvate carboxylase, pyruvate carboxylase, aspartate aminotransferase, homoserine dehydrogenase, aspartate-semialdehyde dehydrogenase, homoserine kinase, threonine synthase, and L-serine dehydratase, are encoded by a polynucleotide derived from the ppc, pyc, aspC, thrA, asd, thrB, thrC and sdaAB genes, respectively, or homologs thereof. In yet another embodiment, to reduce the activity of competing pathways, the recombinant *E. coli* have decreased levels of 2-ketoisovalerate, phenylpyruvate or 2-keto-4-methyl-pentanoate, or any combination thereof, as compared to wild type *E. coli*. The *E. coli* may further include the deletion or inhibition of expression of ldh (e.g., an ldhA), ilvB, ilvI, leuA, leuB, leuC, leuD, poxB, metA, tdh, or pta gene, or any combination thereof, to reduce the activity of competing pathways.

In yet another embodiment, recombinant *E. coli* with substantially reduced alcohol dehydrogenase and/or aldehyde reductase activity that produce phenylacetaldehyde are provided. The recombinant *E. coli* contain mutations in genes adhE, yqhD, adhP, eutG, yiaY, and yjgB and have increased expression or activity of 2-keto-acid decarboxylase. In some embodiments, the recombinant *E. coli* additionally contain mutations in genes eutE, yahK, ybbO, gldA, dkgA/yqhE, and yghA and have increased expression or activity of 2-keto-acid decarboxylase. In some embodiments, the 2-keto-acid decarboxylase is encoded by a polynucleotide derived from a pdc6, aro10, thi3, kivd, and/or pdc gene, or homologs thereof. In one embodiment, the recombinant *E. coli* have increased levels of phenylpyruvate, as compared to wild type *E. coli*. (See FIG. 2) The increased levels of phenylpyruvate can be due to elevated expression or activity of chorismate mutase P/prephenate dehydratase, and chorismate mutase T/prephenate dehydrogenase, as compared to wild type *E. coli*. In one specific embodiment, the chorismate mutase P/prephenate dehydratase is encoded by a polynucleotide derived from a pheA gene, or homologs thereof. In another embodiment, the chorismate mutase T/prephenate dehydrogenase is encoded by a polynucleotide derived from a tyrA gene, or homologs thereof. The *E. coli* may further include the deletion or inhibition of expression of ldh (e.g., an ldhA), frd (e.g., an frdB, an frdC or an frdBC), fnr, ilvE, ilvA, poxB, pflB, leuA or pta gene, or any combination thereof, to reduce the activity of competing pathways.

D. Supplementary Information

The disclosure identifies specific genes useful in the methods, compositions and organisms of the disclosure; however it should be recognized that absolute identity to such genes is not necessary. For example, changes in a particular gene or polynucleotide containing a sequence encoding a polypeptide or enzyme can be performed and screened for activity. Typically such changes include conservative mutation and silent mutations. Such modified or mutated polynucleotides and polypeptides can be screened for expression or function of enzymes using methods known in the art.

Due to the inherent degeneracy of the genetic code, other polynucleotides which encode substantially the same or a functionally equivalent polypeptide can also be used to clone and express the same enzymes. As will be understood by those of skill in the art, it can be advantageous to modify a coding sequence to enhance its expression in a particular host. The genetic code is redundant with 64 possible codons, but most organisms typically use a subset of these codons. The codons that are utilized most often in a species are called optimal codons, and those not utilized very often are classified as rare or low-usage codons. Codons can be substituted to reflect the preferred codon usage of *E. coli*, a process sometimes called "codon optimization" or "controlling for species codon bias." (See Murray et al. 1989 Nucl. Acids Res. 17:477-508)

Those of skill in the art will recognize that, due to the degenerate nature of the genetic code, a variety of DNA compounds differing in their nucleotide sequences can be used to encode a given enzyme of the disclosure. The native DNA sequence encoding the biosynthetic enzymes described above are referenced herein merely to illustrate an embodiment of the disclosure, and the disclosure includes DNA compounds of any sequence that encode the amino acid sequences of the polypeptides and proteins of the enzymes utilized in the methods of the disclosure. In similar fashion, a polypeptide can typically tolerate one or more amino acid substitutions, deletions, and insertions in its amino acid sequence without loss or significant loss of a desired activity. The disclosure includes such polypeptides with different amino acid sequences than the specific proteins described herein so long as they modified or variant polypeptides have the enzymatic anabolic or catabolic activity of the reference polypeptide. Furthermore, the amino acid sequences encoded by the DNA sequences shown herein merely illustrate embodiments of the disclosure.

In addition, homologs of enzymes useful for generating metabolites are encompassed by the microorganisms and methods provided herein. The term "homologs" used with respect to an original enzyme or gene of a first family or species refers to distinct enzymes or genes of a second family or species which are determined by functional, structural or genomic analyses to be an enzyme or gene of the second family or species which corresponds to the original enzyme or gene of the first family or species. Most often, homologs will have functional, structural or genomic similarities. Techniques are known by which homologs of an enzyme or gene can readily be cloned using genetic probes and PCR. Homologs can be identified by reference to various databases and identity of cloned sequences as homolog can be confirmed using functional assays and/or by genomic mapping of the genes.

A protein has "homology" or is "homologous" to a second protein if the nucleic acid sequence that encodes the protein has a similar sequence to the nucleic acid sequence that encodes the second protein. Alternatively, a protein has homology to a second protein if the two proteins have "similar" amino acid sequences. (Thus, the term "homologous proteins" is defined to mean that the two proteins have similar amino acid sequences).

As used herein, two proteins (or a region of the proteins) are substantially homologous when the amino acid sequences have at least about 30%, 40%, 50% 60%, 65%, 70%, 75%, 80%, 85%, 90%, 91%, 92%, 93%, 94%, 95%, 96%, 97%, 98%, or 99% identity. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In one embodiment, the length of a reference sequence aligned for comparison purposes is at least 30%, typically at least 40%, more typically at least 50%, even more typically at least 60%, and even more typically at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences. For example, reference to a kivd gene includes homologs (e.g., pdc6, aro10, thI3, pdc, kdcA, pdcl, pdc5) from other organisms encoding an enzyme having substantially similar enzymatic activity, as well as genes having at least 30, 40, 50, 60, 70, 80, 85, 90, 95, 98, or 99% identity to the referenced gene and which encodes an enzyme having substantially similar enzymatic activity as the referenced gene. For example, pyruvate decarboxylase of *Kluyveromyces lactis* has 37% identity to Kivd at the amino acids level; Kivd from *Lactococcus lactis* and Pdc6 from *Saccharomyces cerevisiae* share 36% identity (Positives=322/562 (57%), Gaps=24/562 (4%)); Kivd from *Lactococcus lactis* and Thi3 from *Saccharomyces cerevisiae* share 32% identity (Positives=307/571 (53%), Gaps=35/571 (6%)); Kivd from *Lactococcus lactis* and Aro10 *Saccharomyces cerevisiae* share 30% identity (Positives=296/598 (49%), Gaps=65/598 (10%)); Aro10 from *Saccharomyces cerevisiae* and Pdc6 from *Saccharomyces cerevisiae* share 34% identity (Positives=320/616 (51%), Gaps=61/616 (9%)); Aro10 from *Saccharomyces cerevisiae* and Thi3 *Saccharomyces cerevisiae* share 30% identity (Positives=304/599 (50%), Gaps=48/599 (8%)); Aro10 from *Saccharomyces cerevisiae* and Pyruvate decarboxylase from *Clostridium acetobutylicum* share 30% identity (Positives=291/613 (47%), Gaps=73/613 (11%)); Pdc6 from *Saccharomyces cerevisiae* and Thi3 from *Saccharomyces cerevisiae* share 50% identity (Positives=402/561 (71%), Gaps=17/561 (3%)); Pdc6 from *Saccharomyces cerevisiae* and Pyruvate decarboxylase from *Clostridium acetobutylicum* share 38% identity (Positives=328/570 (57%), Gaps=30/570 (5%)); and Thi3 from *Saccharomyces cerevisiae* and Pyruvate decarboxylase from *Clostridium acetobutylicum* share 35% identity (Positives=284/521 (54%), Gaps=25/521 (4%)). Sequence for each of the genes and polypeptides/enzymes listed herein can be readily identified using databases available on the World-Wide-Web (see, e.g., eecoli.kaist.ac.kr/main.html). In addition, the amino acid sequence and nucleic acid sequence can be readily compared for identity using commonly used algorithms in the art.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology is adjusted upwards to correct for the conservative nature of the substitution. Means for making this adjustment are well known to those of skill in the art (see, e.g., Pearson et al., 1994, hereby incorporated herein by reference).

Method for Producing *E. coli* with Substantially Reduced Alcohol Dehydrogenase Activity and/or Reduced Isobutyraldehyde Reductase Activity In one embodiment, the methods for producing *E. coli* with substantially reduced alcohol dehydrogenase and/or aldehyde reductase activity include targeted genetic modification of the adhE, yqhD, adhP, eutG, yiaY, and yjgB genes. In another embodiment, the methods for producing *E. coli* with substantially reduced isobutyraldehyde reductase activity include targeted genetic modification of the adhE, yqhD, adhP, eutG, fucO, and yjgB genes. In another embodiment, the methods for producing *E. coli* with even more substantially reduced isobutyraldehyde reductase activity include targeted genetic modification of the adhE, yqhD, adhP, eutG, fucO, yjgB eutE, yahK, ybbO, gldA, dkgA/yqhE, and yghA genes. The genetic modifications of the enzymes decrease the activity of enzymes by 70%, 75%, 80%, 85%, 90%, 95%, 98%, 99% or 100% relative to wild type enzymes. Genetic modifications that reduce or eliminate the activity of enzymes may include point mutations that cause amino acid changes in the enzymes, deletion mutations, nonsense mutations, frameshift mutations, sequence duplication or inversions and insertions. Mutations can be introduced by molecular biology means, such as homologous recombinations, antisense technologies or RNA interference, or by chemical means, such as treatments with DNA intercalators or DNA methylating agents followed by a secondary screening step wherein the strains are selected for substantially decreased alcohol dehydrogenase activity or isobutyraldehyde reductase activity.

In one embodiment, methods of producing recombinant *E. coli* with substantially reduced alcohol dehydrogenase and/or aldehyde reductase activity that convert a suitable substrate or metabolic intermediate to aldehydes are provided. The method includes generating recombinant *E. coli* strains with mutations in genes adhE, yqhD, adhP, eutG, yiaY, and yjgB and transforming the *E. coli* with one or more recombinant polynucleotides encoding polypeptides having 2-keto-acid decarboxylase activity.

In another embodiment, methods of producing recombinant *E. coli* with substantially reduced isobutyraldehyde reductase activity that convert a suitable substrate or metabolic intermediate to isobutyraldehyde are provided. The method includes generating recombinant *E. coli* strains with mutations in genes adhE, yqhD, adhP, eutG, fucO, and yjgB and transforming the *E. coli* with one or more recombinant polynucleotides encoding polypeptides having 2-keto-acid decarboxylase activity.

In another embodiment, methods of producing recombinant *E. coli* with even more substantially reduced isobutyraldehyde reductase activity that convert a suitable substrate or metabolic intermediate to isobutyraldehyde are provided. The method includes generating recombinant *E. coli* strains with mutations in genes adhE, yqhD, adhP, eutG, fucO, yjgB, adhE, yqhD, adhP, eutG, fucO, yjgB eutE, yahK, ybbO, gldA, dkgA/yqhE, and yghA and transforming the *E. coli* with one or more recombinant polynucleotides encoding polypeptides having 2-keto-acid decarboxylase activity.

In one specific embodiment, methods of producing recombinant *E. coli* with substantially reduced alcohol dehydrogenase and/or aldehyde reductase activity that convert a suitable substrate or metabolic intermediate to isobutyraldehyde are provided. The methods include generating recombinant *E. coli* strains with mutations in genes adhE, yqhD, adhP, eutG, yiaY, and yjgB and transforming the *E. coli* with one or more recombinant polynucleotides encoding polypeptides having 2-keto-acid decarboxylase activity. The method can further include transforming *E. coli* with one or more recombinant polynucleotides encoding polypeptides having acetohydroxy acid synthase activity or acetolactate synthase activity, acetohydroxy acid isomeroreductase activity, and dihydroxyacid dehydratase activity.

In another specific embodiment, methods of producing recombinant *E. coli* with substantially reduced isobutyraldehyde reductase activity that convert a suitable substrate or metabolic intermediate to isobutyraldehyde are provided. The methods include generating recombinant *E. coli* strains with mutations in genes adhE, yqhD, adhP, eutG, fucO, and yjgB and transforming the *E. coli* with one or more recombinant polynucleotides encoding polypeptides having 2-keto-acid decarboxylase activity. The method can further include transforming *E. coli* with one or more recombinant polynucleotides encoding polypeptides having acetohydroxy acid synthase activity or acetolactate synthase activity, acetohydroxy acid isomeroreductase activity, and dihydroxyacid dehydratase activity.

In another specific embodiment, methods of producing recombinant *E. coli* with even more substantially reduced isobutyraldehyde reductase activity that convert a suitable substrate or metabolic intermediate to isobutyraldehyde are provided. The methods include generating recombinant *E. coli* strains with mutations in genes adhE, yqhD, adhP, eutG, fucO, yjgB, adhE, yqhD, adhP, eutG, fucO, yjgB eutE, yahK, ybbO, gldA, dkgA/yqhE, and yghA and transforming the *E. coli* with one or more recombinant polynucleotides encoding polypeptides having 2-keto-acid decarboxylase activity. and transforming the *E. coli* with one or more recombinant polynucleotides encoding polypeptides having 2-keto-acid decarboxylase activity. The method can further include transforming the *E. coli* with one or more recombinant polynucleotides encoding polypeptides having acetohydroxy acid synthase activity or acetolactate synthase activity, acetohydroxy acid isomeroreductase activity, and dihydroxyacid dehydratase activity.

In another specific embodiment, methods of producing recombinant *E. coli* with substantially reduced alcohol dehydrogenase and/or aldehyde reductase activity that convert a suitable substrate or metabolic intermediate to butyraldehyde are provided. The methods include generating recombinant *E. coli* strains with mutations in genes adhE, yqhD, adhP, eutG, yiaY, and yjgB and transforming the *E. coli* with one or more recombinant polynucleotides encoding polypeptides having 2-keto-acid decarboxylase activity. The method can further include transforming *E. coli* with one or more recombinant polynucleotides encoding polypeptides having α-isopropylmalate synthase activity, β-isopropylmalate dehydrogenase activity, α-isopropylmalate isomerase activity, and threonine dehydratase activity.

In one embodiment, methods of producing recombinant *E. coli* with substantially reduced alcohol dehydrogenase and/or aldehyde reductase activity that convert a suitable substrate or metabolic intermediate to 2-methyl-butyraldehyde are provided. The methods include generating recombinant *E. coli* strains with mutations in genes adhE, yqhD, adhP, eutG, yiaY, and yjgB and transforming the *E. coli* with one or more recombinant polynucleotides encoding polypeptides having 2-keto-acid decarboxylase activity. The method can further include transforming *E. coli* with one or more recombinant polynucleotides encoding polypeptides having threonine dehydratase activity, acetohydroxy acid synthase activity or acetolactate synthase activity, acetohydroxy acid isomeroreductase activity, and dihydroxy-acid dehydratase activity.

In another embodiment, methods of producing recombinant *E. coli* with substantially reduced alcohol dehydrogenase and/or aldehyde reductase activity that convert a suitable substrate or metabolic intermediate to 3-methyl-butyraldehyde are provided. The methods include generating recombinant *E. coli* strains with mutations in genes adhE, yqhD, adhP, eutG, yiaY, and yjgB and transforming *E. coli* with one or more recombinant polynucleotides encoding polypeptides having 2-keto-acid decarboxylase activity. The method can further include transforming the *E. coli* with one or more recombinant polynucleotides encoding polypeptides having acetohydroxy acid synthase activity or acetolactate synthase activity, acetohydroxy acid isomeroreductase activity, dihydroxy-acid dehydratase activity, α-isopropylmalate synthase activity, α-isopropylmalate isomerase activity, and β-isopropylmalate dehydrogenase activity.

In another embodiment, methods of producing recombinant *E. coli* with substantially reduced alcohol dehydrogenase and/or aldehyde reductase activity that convert a suitable substrate or metabolic intermediate to propionaldehyde are provided. The methods include generating recombinant *E. coli* strain with mutations in genes adhE, yqhD, adhP, eutG, yiaY, and yjgB and transforming the *E. coli* with one or more recombinant polynucleotides encoding polypeptides having 2-keto-acid decarboxylase activity. The method can further include transforming *E. coli* with one or more recombinant polynucleotides encoding polypeptides having threonine dehydratase activity.

In another embodiment, methods of producing recombinant *E. coli* with substantially reduced alcohol dehydrogenase and/or aldehyde reductase activity that convert a suitable substrate or metabolic intermediate to phenylacetaldehyde are provided. The method includes generating recombinant *E. coli* strains with mutations in genes adhE, yqhD, adhP, eutG, yiaY, and yjgB and transforming the *E. coli* with one or more recombinant polynucleotides encoding polypeptides having 2-keto-acid decarboxylase activity. The method can further include transforming *E. coli* with one or more recombinant polynucleotides encoding polypeptides having chorismate mutase P/prephenate dehydratase activity, and chorismate mutase T/prephenate dehydrogenase activity.

Although *E. coli* was utilized in exemplary embodiments, the present disclosure is not limited to this genus and species of bacteria. It is understood that a range of bacteria can be modified to possess substantially reduced alcohol dehydrogenase (ADH) and/or aldehyde reductase activity for the production of aldehydes or non-alcohol chemicals. It is also understood that various microorganisms can act as "sources" for genetic material encoding target enzymes suitable for use in recombinant bacteria provided herein. In some embodiments, the recombinant bacteria are gram-negative bacteria, while in other embodiments, the recombinant bacteria are gram-positive bacteria.

The term "bacteria" refers to a domain of prokaryotic organisms. Bacteria include at least 11 distinct groups as follows: (1) Gram-positive (gram+) bacteria, of which there are two major subdivisions: (1) high G+C group (Actinomycetes, Mycobacteria, Micrococcus, others) (2) low G+C group (*Bacillus*, Clostridia, *Lactobacillus*, Staphylococci, Streptococci, Mycoplasmas); (2) Proteobacteria, e.g., Purple photosynthetic+non-photosynthetic Gram-negative bacteria (includes most "common" Gram-negative bacteria); (3)

Cyanobacteria, e.g., oxygenic phototrophs; (4) Spirochetes and related species; (5) *Planctomyces*; (6) Bacteroides, Flavobacteria; (7) Chlamydia; (8) Green sulfur bacteria; (9) Green non-sulfur bacteria (also anaerobic phototrophs); (10) Radioresistant micrococci and relatives; (11) Thermotoga and Thermosipho thermophiles.

"Gram-negative bacteria" include cocci, nonenteric rods, and enteric rods. The genera of Gram-negative bacteria include, for example, *Neisseria, Spirillum, Pasteurella, Brucella, Yersinia, Francisella, Haemophilus, Bordetella, Escherichia, Salmonella, Shigella, Klebsiella, Proteus, Vibrio, Pseudomonas, Bacteroides, Acetobacter, Aerobacter, Agrobacterium, Azotobacter, Spirilla, Serratia, Vibrio, Rhizobium, Chlamydia, Rickettsia, Treponema,* and *Fusobacterium.*

"Gram positive bacteria" include cocci, nonsporulating rods, and sporulating rods. The genera of gram positive bacteria include, for example, *Actinomyces, Bacillus, Clostridium, Corynebacterium, Erysipelothrix, Lactobacillus, Listeria, Mycobacterium, Myxococcus, Nocardia, Staphylococcus, Streptococcus,* and *Streptomyces.*

The terms "recombinant bacteria," and "recombinant host cell" and "host" are used interchangeably herein to refer to bacteria that have been genetically modified. Desirable genetic modifications result in the over-expression of endogenous enzymes, the expression of non-endogenous enzymes, and/or the elimination of endogenous enzymes, in some embodiments, recombinant bacteria contain mutations in specific genes (e.g., deletion of an endogenous gene). The *E. coli* gene name is used throughout in reference to deleted genes for the sake of simplicity because this bacterium has been extensively characterized. The present disclosure, however, is not limited to *E. coli*. Accordingly, when the recombinant bacteria is of a different genus or species, the deleted gene of interest is a homolog or ortholog of the *E. coli* gene.

TABLE I

Deleted Genes

| Deleted Gene(s) | EcoGene No. | NCBI No. Enzyme | Isobutyraldehyde Reductase |
|---|---|---|---|
| ldhA (htpH, hslF, hslI) | EG13186 | NP_415898 | – |
| frdABCD | EG10330 | YP_492299.1 | – |
|  | EG10331 | YP_492298.1 |  |
|  | EG10332 | YP_492297.1 |  |
|  | EG10333 | YP_492296.1 |  |
| pta | EG20173 | YP_490539.1 | – |
| fnr (frdB, nirA, nirR, ossA, oxrA) | EG10325 | YP_489604.1 | – |
| pflB (pfl) | EG10701 | YP_489175.1 | – |
| adhE (adhC, ana) | EG10031 | NP_415757 | – |
| yqhD | EG13014 | NP_417484 | + |
| adhP (yddN) | EG12622 | NP_415995 | + |
| eutG (yffV) | EG14183 | NP_416948 | + |
| yiaY | EG12293 | YP_026233 | – |
| yjgB (ahr) | EG11436 | NP_418257 | + |
| betA | EG10109 | NP_414845 | – |
| fucO | EG10351 | NP_417279 | + |
| eutE (yffX) | EG14185 | NP_416950 | – |
| yahK | EG13595 | NP_414859 | + |
| ybbO | EG13262 | NP_415026 | + |
| dkgA (yqhE, AKR5C2) | EG13015 | NP_417485 | + |
| gldA | EG11904 | NP_418380 | + |
| yghA | EG11292 | NP_417476 | + |

TABLE II

Inserted Genes

| Inserted Gene | Source | EcoGene No. | NCBI No. Enzyme |
|---|---|---|---|
| kivd | *L. lactis* | — | CAG34226.1 |
| alsS | *B. subtilis* | — | CAB07802.1 |
| ilvC | *E. coli* | EG10495 | NP_418222 |
| ilvD | *E. coli* | EG10496 | YP_026248 |
| leuA |  | EG11226 | YP_488380.1 |
| leuCD |  | EG11576 | YP_488378.1 |
|  |  | EG11575 | YP_488377.1 |
| leuB |  | EG11577 | YP_488379.1 |
| ilvA |  | EG10493 | YP_491666.1 |
| pheA |  | EG10707 | YP_490822.1 |
| tyrA |  | EG11039 | YP_490823.1 |

Table I provides accession numbers of genes that have been deleted from various recombinant bacteria of the present disclosure, while Table II provides accession numbers of the genes that have been inserted in various recombinant bacteria of the present disclosure.

General Methods for Producing Non-Alcohol Chemicals

In one embodiment, the methods for the production of non-alcohol chemicals include the step of growing recombinant bacteria such as *E. coli* in the presence of a suitable carbon source or metabolic intermediate. Suitable carbon sources may include, but are not limited to, glucose, glycerol, sugars, starches, and lignocellulosics, including glucose derived from cellulose and $C_5$ sugars derived from hemicellulose, such as xylose.

In another embodiment, methods for producing aldehydes are provided. The methods include providing recombinant *E. coli* or other bacteria; culturing the *E. coli* or other bacteria in the presence of a suitable substrate or metabolic intermediate and under conditions suitable for the conversion of the substrate to aldehydes; and substantially purifying the aldehydes. In various embodiments, the aldehyde produced is isobutyraldehyde, butyraldehyde, 2-methyl-butyraldehyde, 3-methyl-butyraldehyde, propionaldehyde, or phenylacetaldehyde.

Methods for Purifying Higher Aldehydes from the Culture Medium of *E. coli*

Both product recovery efficiency and productivity are key factors for producing organic chemicals with recombinant bacteria such as *E. coli*. Product removal in situ can largely eliminate the cytotoxic effect of the produced chemicals and thereby improve both the recovery efficiency and productivity.

Chemicals with low boiling point and high vapor pressure can be readily stripped from the culture medium during production. In one specific embodiment, the methods for purifying higher aldehydes produced from recombinant *E. coli* or other bacteria include removing the aldehydes from the production medium by bubbling of air. In one embodiment, the aldehyde produced and collected by bubbling of air is isobutyraldehyde, butyraldehyde, or propionaldehyde. The evaporated aldehydes can be further condensed to a desirable concentration. In one specific embodiment, the evaporated aldehyde is condensed using a Graham condenser.

In other embodiments, the aldehydes have low solubility in water and can be directly collected from production culture. In one specific embodiment, the aldehyde that can be directly collected is 2-methyl-butyraldehyde, 3-methyl-butyraldehyde, or phenylacetaldehyde.

EXAMPLES

The following examples are merely illustrative and are not meant to limit any embodiments of the present disclosure in any way.

Materials and Methods
Reagents and Bacterial Strains

Restriction enzymes and Antarctic phosphatase were from New England Biolabs (Ipswich, Mass., USA). Rapid DNA ligation kit was from Roche (Mannheim, Germany). KOD DNA polymerase was from EMD Chemicals (San Diego, Calif., USA). Oligonucleotides were from Integrated DNA Technologies (San Diego, Calif., USA).

TABLE 1

E. coli Strains and Plasmids.

| Strain/Plasmid | Description |
|---|---|
| BW25113 | rrnBT14 ΔlacZWJ16 hsdR514 ΔaraBADAH33 ΔrhaBADLD78 |
| JCL16 | BW25113 F'[traD36 proAB+ lacI$^q$ZΔM15] |
| JCL260 | Same as JCL16 but ΔadhE Δfnr-ΔldhA ΔfrdBC ΔpflB Δpta |
| AL345 | JCL260 with plasmids pGR03 and pSA129 |
| AL80 | Same as JCL260 but ΔyqhD |
| AL275 | AL80 with plasmids pSA69 and pSA129 |
| AL287 | Same as JCL260 but ΔyqhD ΔadhP |
| AL293 | AL287 with plasmids pGR03 and pSA129 |
| AL288 | Same as JCL260 but ΔyqhD ΔeutG |
| AL294 | AL288 with plasmids pGR03 and pSA129 |
| AL289 | Same as JCL260 but ΔyqhD ΔyiaY |
| AL295 | AL289 with plasmids pGR03 and pSA129 |
| AL290 | Same as JCL260 but ΔyqhD ΔyjgB |
| AL296 | AL290 with plasmids pGR03 and pSA129 |
| AL312 | Same as JCL260 but ΔyqhD ΔadhP ΔeutG |
| AL313 | AL312 with plasmids pGR03 and pSA129 |
| AL322 | Same as JCL260 but ΔyqhD ΔadhP ΔeutG ΔyiaY |
| AL328 | AL322 with plasmids pGR03 and pSA129 |
| AL331 | Same as JCL260 but ΔyqhD ΔadhP ΔeutG ΔyiaY ΔyjgB |
| AL332 | AL331 with plasmids pGR03 and pSA129 |
| AL555 | Same as JCL260 but ΔyqhD ΔbetA |
| AL556 | Same as JCL260 but ΔyqhD ΔadhP ΔeutG ΔyiaY ΔyjgB ΔbetA |
| AL615 | Same as JCL260 but ΔyqhD ΔfucO |
| AL616 | Same as JCL260 but ΔyqhD ΔeutE |
| AL626 | Same as JCL260 but ΔyqhD ΔadhP ΔeutG ΔyiaY ΔyjgB ΔbetA ΔfucO |
| AL627 | AL626 with plasmids pGR03 and pSA129 |
| AL707 | Same as JCL260 but ΔyqhD ΔadhP ΔeutG ΔyiaY ΔyjgB ΔbetA ΔfucO ΔeutE |
| AL1448 | Same as AL626 but ΔeutE ΔyahK ΔybbO ΔgldA ΔdkgA ΔyghA |
| pSA69 | p15A ori; Kan$^R$; P$_L$lacO$_1$: alsS-ilvCD |
| pSA129 | ColE1 ori; Amp$^R$; P$_L$lacO$_1$: kivd |
| pSA138 | ColE1 ori; P$_L$lacO$_1$: kivd-yqhD |
| pGR03 | Same as pSA69 but Cm$^R$ |
| pAL217 | ColE1 ori; Amp$^R$; P$_L$lacO$_1$: kivd-adhP |
| pAL218 | ColE1 ori; Amp$^R$; P$_L$lacO$_1$: kivd-eutG |
| pAL219 | ColE1 ori; Amp$^R$; P$_L$lacO$_1$: kivd-yiaY |
| pAL220 | ColE1 ori; Amp$^R$; P$_L$lacO$_1$: kivd-yjgB |
| pAL221 | ColE1 ori; Amp$^R$; P$_L$lacO$_1$: kivd-betA |
| pAL222 | ColE1 ori; Amp$^R$; P$_L$lacO$_1$: kivd-fucO |
| pAL223 | ColE1 ori; Amp$^R$; P$_L$lacO$_1$: kivd-eutE |
| pZE12-luc | ColE1 ori; Amp$^R$; P$_L$lacO$_1$: luc(VF) |
| pAL162 | ColE1 ori; Amp$^R$; P$_L$lacO$_1$: adhP |
| pAL158 | ColE1 ori; Amp$^R$; P$_L$lacO$_1$: eutG |
| pAL157 | ColE1 ori; Amp$^R$; P$_L$lacO$_1$: yiaY |
| pAL156 | ColE1 ori; Amp$^R$; P$_L$lacO$_1$: yjgB |
| pAL213 | ColE1 ori; Amp$^R$; P$_L$lacO$_1$: betA |
| pAL214 | ColE1 ori; Amp$^R$; P$_L$lacO$_1$: fucO |
| pAL215 | ColE1 ori; Amp$^R$; P$_L$lacO$_1$: eutE |

Cell Culture

For standard culturing purposes, E. coli was grown in 5-20 mL of LB media containing any required antibiotics at 37° C. with shaking at 250 rpm in a rotary shaker. For production experiments, E. coli was cultured in 20 ml M9 media containing 36 g/l glucose and 5 g/l yeast extract. The cells were cultured at 37° C. for 24 h in a rotary shaker (250 rpm). Cells were further induced with IPTG at OD$_{600nm}$ 0.4.

Example 1: Recombinant E. coli which Produce Isobutanol

Figure 3:
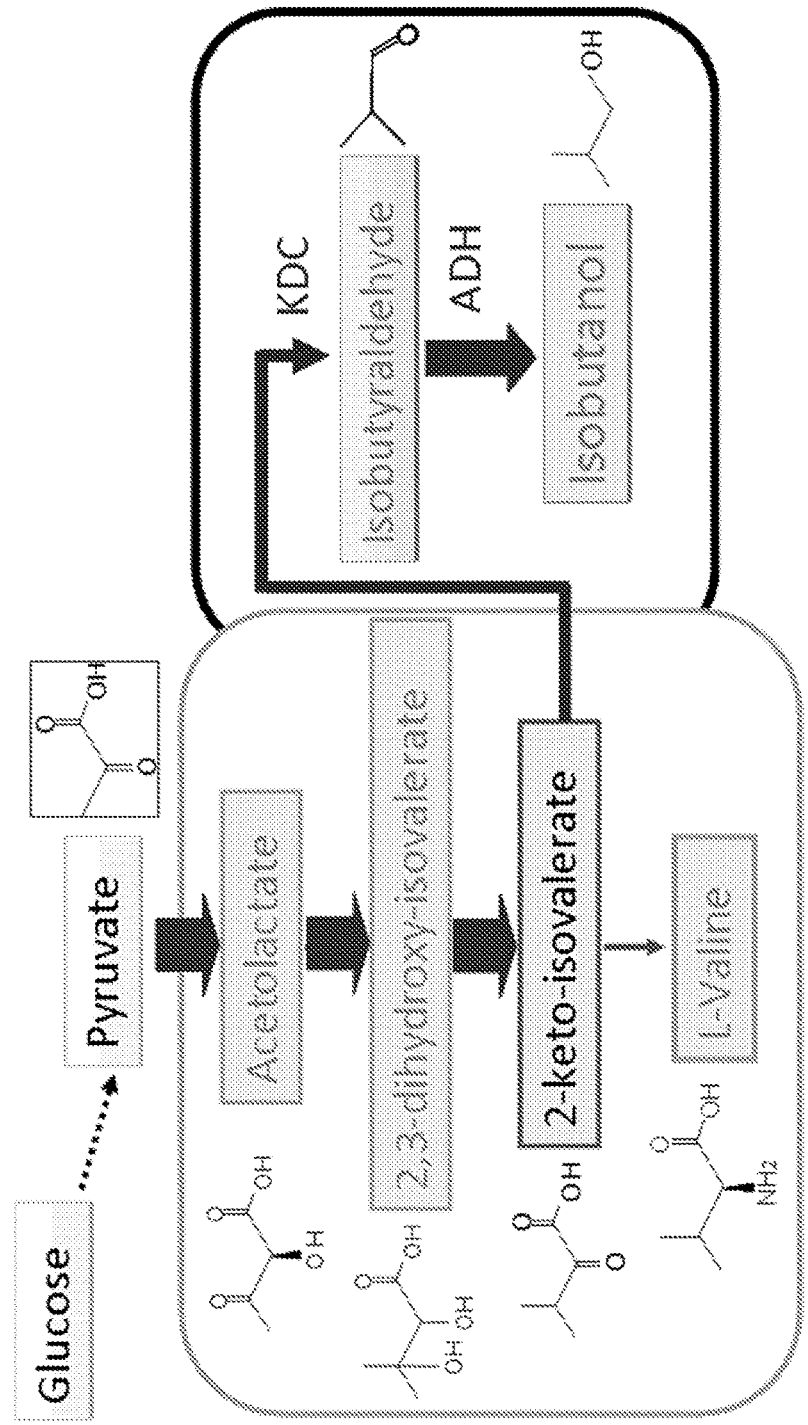
FIG. 3 illustrates the pathway for producing isobutyraldehyde and isobutanol in *E. coli*. KDC: 2-keto-acid decarboxylase; ADH: Alcohol dehydrogenase.
Figure 4:
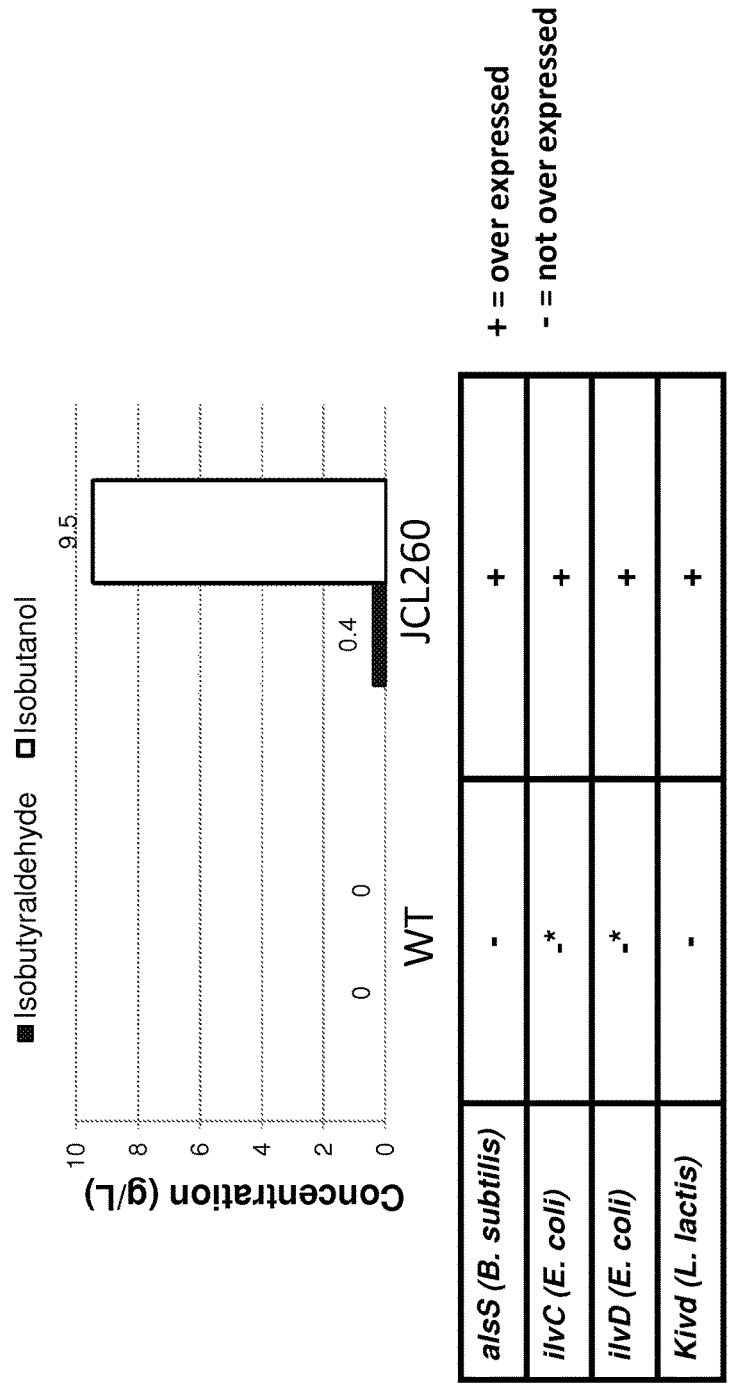
FIG. 4 illustrates that *E. coli* do not naturally produce isobutanol or isobutyraldehyde. Overexpression of the 2-keto-acid decarboxylase kivd and valine biosynthesis genes including alsS, ilvC and ilvD in *E. coli* enables significant isobutanol production and trace amount of isobutyraldehyde production.

Wild type E. coli cannot produce isobutanol or its precursor isobutyraldehyde because they lack the 2-keto-acid decarboxylase (KDC) that converts 2-keto-isovalerate to isobutyraldehyde (FIG. 3). When kivd, a KDC, was overexpressed in E. coli together with the valine biosynthesis genes, including alsS (B. subtilis), ilvC (E. coli) and ilvD (E. coli), significant amounts of isobutanol were produced (FIG. 4). Overexpression of the valine biosynthesis genes was not necessary for isobutanol production but it amplified the endogenous pathway and promoted the efficient conversion of a carbon source to 2-keto-isovalerate. To optimize production of isobutanol, the E. coli strain JCL260 was used as the production host. This strain has deletions in fnr, ldhA, frdBC, pflB, pta, all of which are genes involved in byproduct formation. JCL260 also has a deletion in adhE, one of E. coli's six ADH genes. The other five ADH genes are yqhD, adhP, eutG, yiaY, and yjgB. Since these endogenous ADHs together efficiently convert isobutyraldehyde to isobutanol, very little isobutyraldehyde was produced.

Example 2: Engineering E. coli to Produce Isobutyraldehyde

Figure 5:
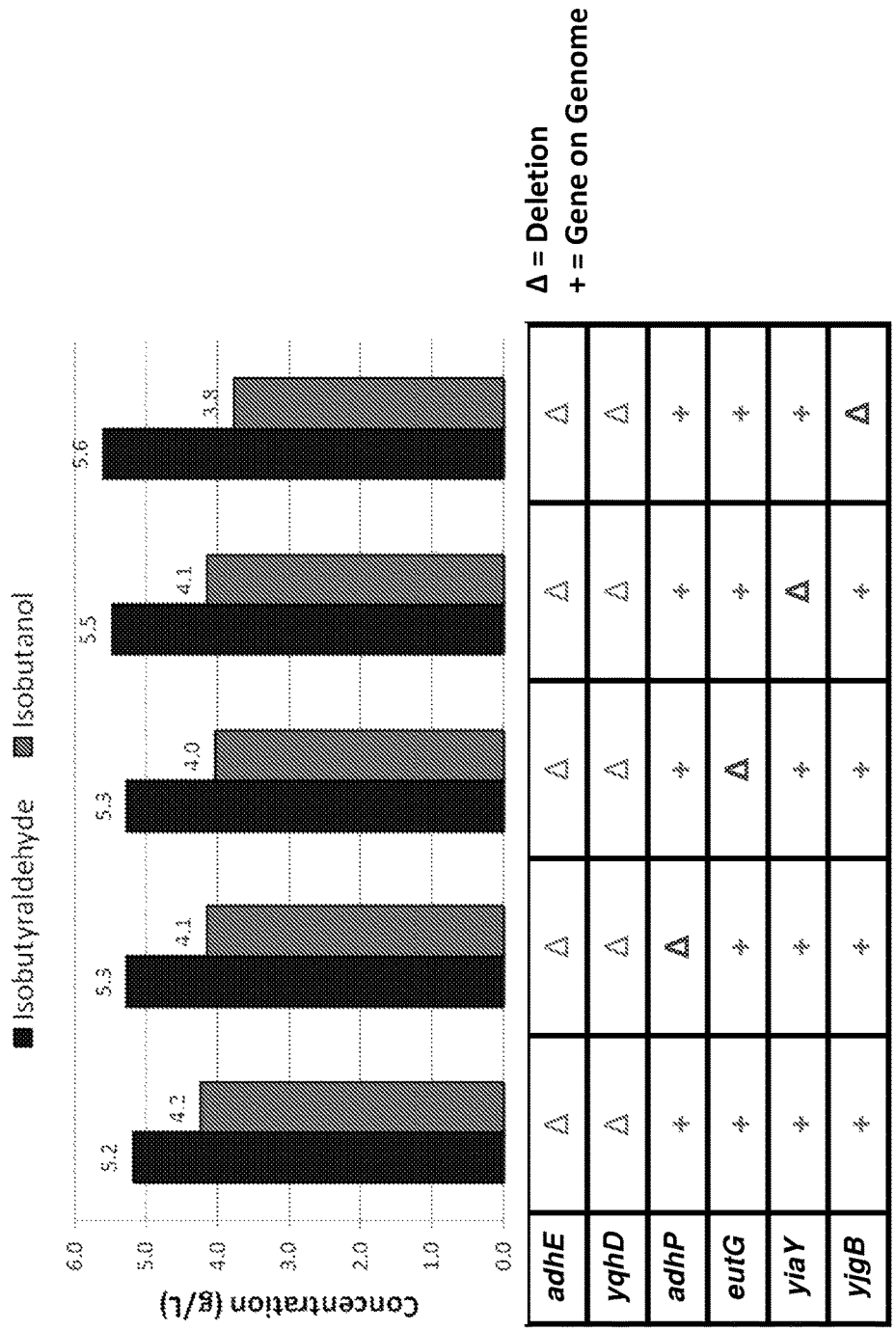
FIG. 5 illustrates that deletion of adhP, eutG, yiaY, or yjgB in combination with deletions of adhE and yqhD does not significantly affect the production of isobutyraldehyde or isobutanol as compared to a ΔadhE and ΔyqhD strain.
Figure 6:
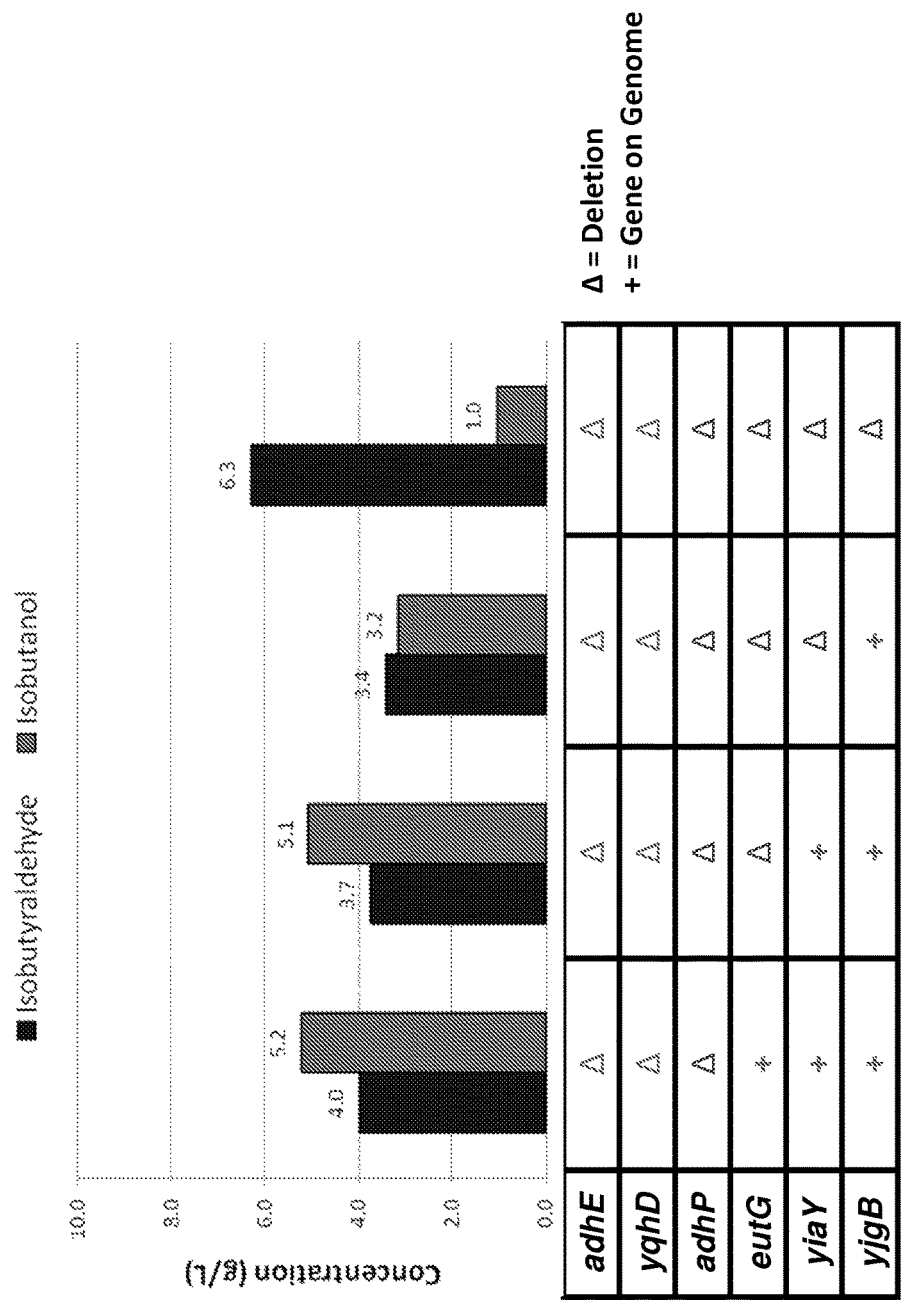
FIG. 6 shows that *E. coli* strains with deletions of five or less of the ADH genes (ΔadhE, ΔyqhD, ΔadhP, ΔeutG, ΔyiaY) still have significant amount of alcohol dehydrogenase/isobutyraldehyde reductase activity, as shown by the production of isobutanol. This activity is substantially reduced in the strain where all six ADHs are deleted (ΔadhE, ΔyqhD, ΔadhP, ΔeutG, ΔyiaY, and ΔyjgB).
Figure 7:
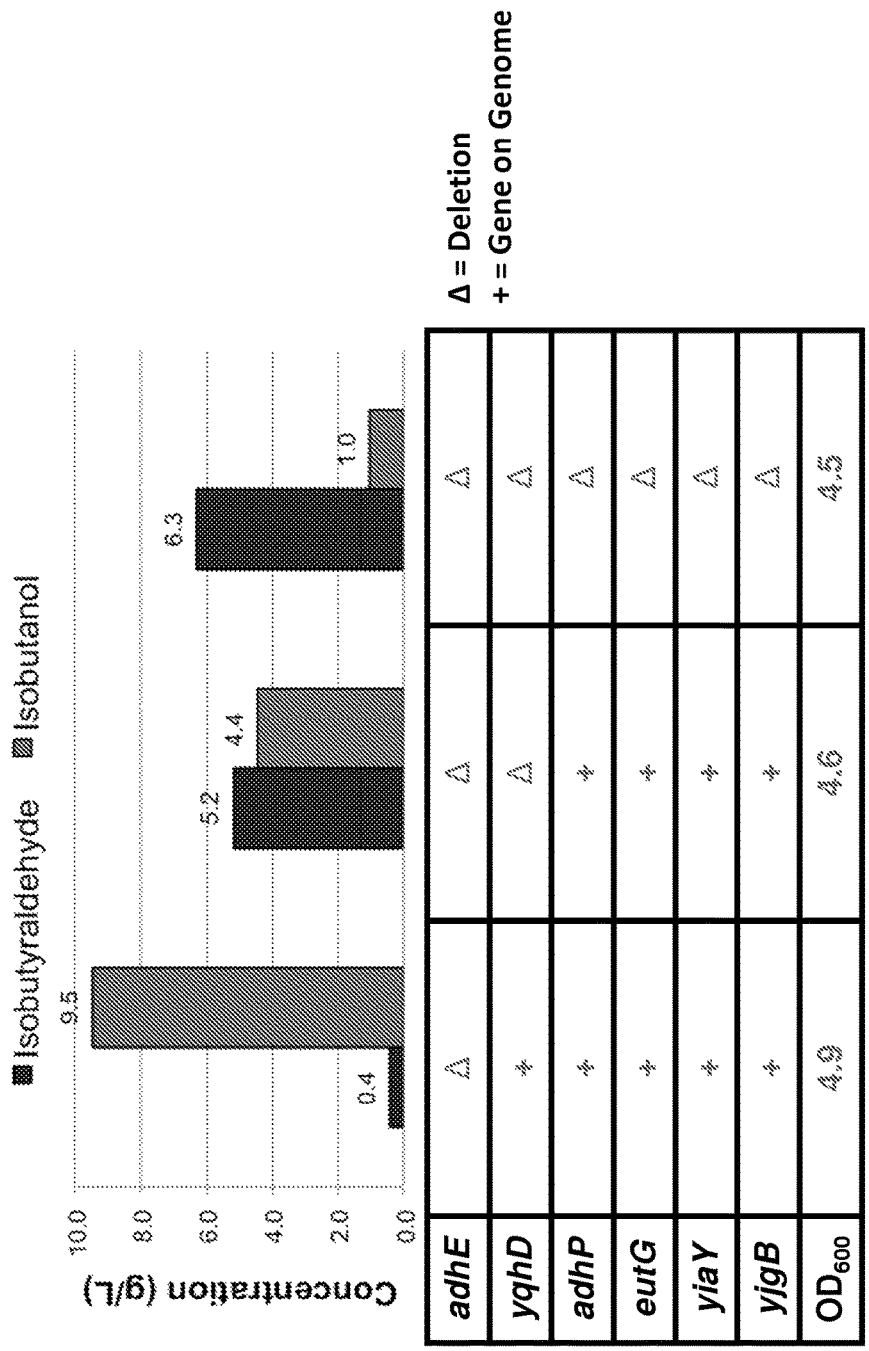
FIG. 7 shows results confirming that the six ADH genes (adhE, yqhD, adhP, eutG, yiaY, yjgB) together contribute to the majority of alcohol dehydrogenase/isobutyraldehyde reductase activity in *E. coli*.

The same JCL260 strain described above was further modified for isobutyraldehyde production. More ADH genes were deleted to reduce the conversion of isobutyraldehyde to isobutanol. Among the five ADH genes, yqhD was known to contribute significantly to the alcohol dehydrogenase/isobutyraldehyde reductase activity in E. coli (Atsumi, Appl Microbiol Biotechnol, 2010). In order to examine the function of the other four ADH genes, JCL260 with ΔyqhD was further modified to delete another ADH gene selected from adhP, eutG, yiaY, and yjgB. The production of isobutyraldehyde and isobutanol of these strains was measured. It was found that the extra single deletion only had negligible effect on the production of the chemicals (FIG. 5). In order to examine the possibility of redundancy among these ADH genes, a series of multiple deletion mutants were generated and tested for the production of isobutyraldehyde and isobutanol (FIG. 6). It appeared that the alcohol dehydrogenase/isobutyraldehyde reductase activity in E. coli was substantially eliminated and the production ratio of isobutyraldehyde to isobutanol was significantly increased only when all six ADH genes were deleted (FIG. 6). The experiments were repeated and results were statistically significant (FIG. 7 and Table 2). Together, these data suggested that: first, the six ADH genes contribute to majority of the alcohol dehydrogenase/isobutyraldehyde reductase activity in E. coli; second, these genes share high degree of redundancy and multiple deletions or mutations are required to obtain a strain with substantially reduced alcohol dehydrogenase/isobutyraldehyde reductase activity. Therefore, strains in which four, five or six ADH genes are deleted or mutated to be less active or inactive can be used to achieve increased production of isobutyraldehyde in E. coli.

Figure 8:
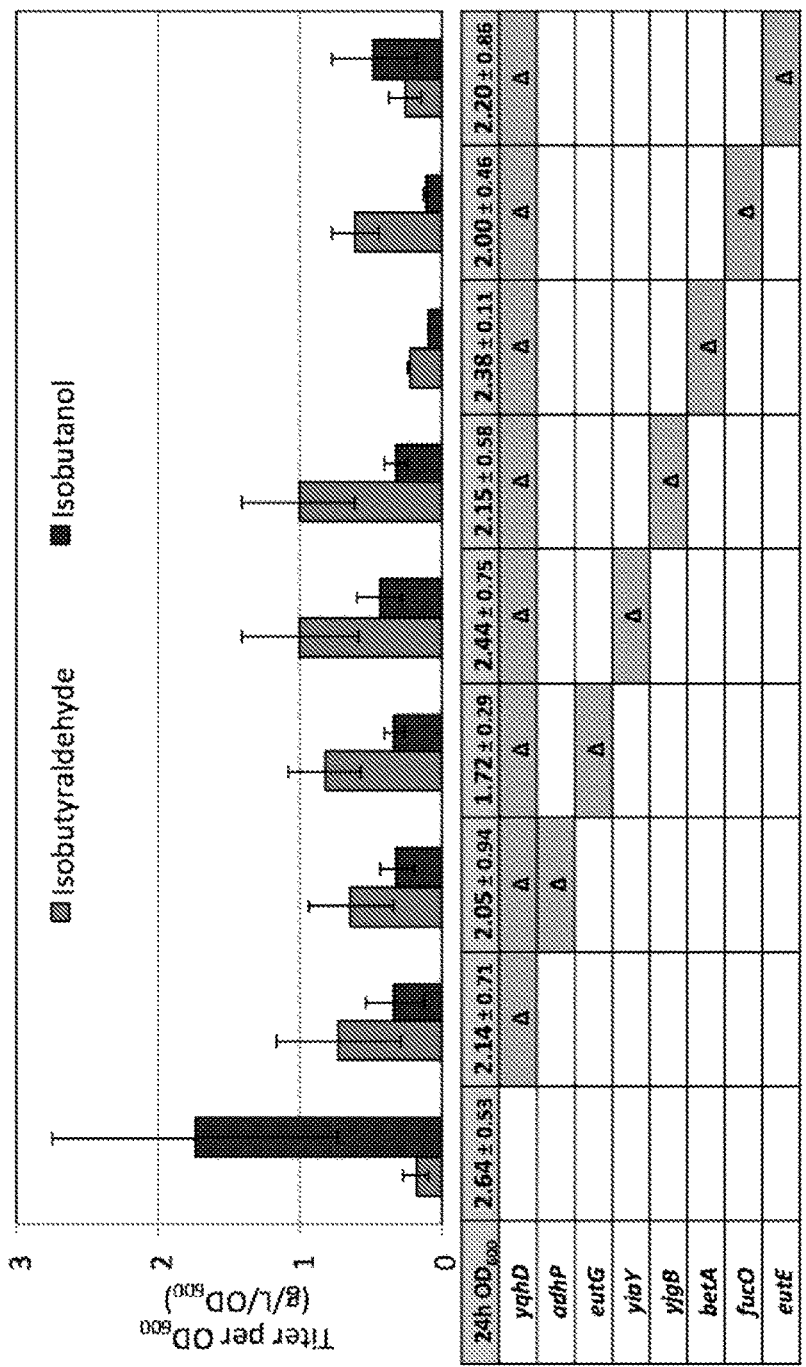
FIG. 8 illustrates the effects of combined deletions of alcohol dehydrogenase and/or isobutyraldehyde reductase genes in *E. coli*. Delta (Δ) indicates deletion of a gene. All strains contained pGR03 (alsS, ilvC, and ilvD) and pSA129 (kivd).
Figure 9:
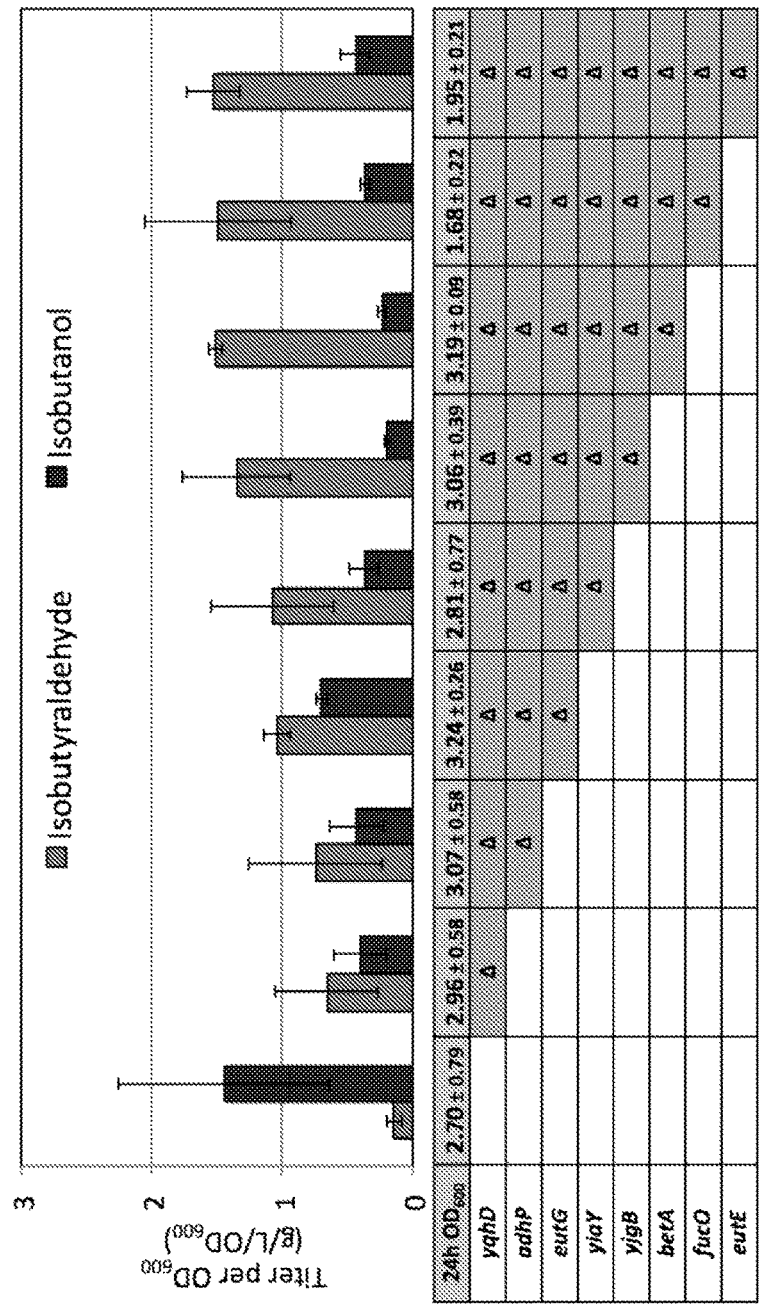
FIG. 9 illustrates the effects of combined deletions of alcohol dehydrogenase and/or isobutyraldehyde reductase genes in *E. coli*. Delta (Δ) indicates deletion of a gene. All strains contained pGR03 (alsS, ilvC, and ilvD) and pSA129 (kivd). Combinatorial deletions of additional ADH or IBR genes contribute to increased production of isobutyraldehyde and decreased production of isobutanol.

A known isobutyraldehyde reductase (IBR) gene, yqhD, as well as candidate isobutyraldehyde reductase genes, adhP, eutG, yiaY, yjgB, betA, fucO, and eutE, were cloned onto individual plasmids downstream of kivd and introduced into AL626, which also contained pGR03. The resulting recombinant *E. coli* overexpressed the above mentioned gene products and were screened for changes in isobutyraldehyde reductase activity as measured by the production of both isobutyraldehyde and isobutanol. Overexpression of yqhD, adhP, eutG, yjgB, and fucO significantly increased the production of isobutanol relative to isobutyraldehyde, suggesting that these genes are indeed functionally active isobutyraldehyde reductases. AL626 was modified to introduce deletions in adhE, yqhD, adhP, eutG, yiaY, yjgB, betA, and fucO and incorporate pGR03 and pSA129. This recombinant strain (AL627), containing deletions in multiple alcohol dehydrogenases and isobutyraldehyde reductases, accumulated significantly higher amounts of isobutyraldehyde relative to the control strain JC260, as well as consequently lower levels of isobutanol (FIGS. 8 and 9). Therefore, strains in which four, five or six IBR genes are deleted or mutated to be less active or inactive can be used to achieve increased production of isobutyraldehyde in *E. coli*.

Gas Chromatography was performed using a Shimadzu GC-2010 with an AOC-20s auto sampler. Column used is a 30 m×0.32 mm, 0.50 µm film thickness, DB-wax column from Agilent Technologies. Column settings were programmed as follows: held at 40° C. for 3 min, then temperature increased at a rate of 45° C./min until 235° C., then held at 235° C. for 3 minutes. Injection volume was 0.5 µL. Under these conditions, retention times for isobutyraldehyde, ethanol, isobutanol, and 1-pentanol were 1.389 min, 2.569 min, 4.423 min, and 5.387 min, respectively.

Standard samples were prepared by diluting 10 g/L stock solution of desire compounds to 1 g/L in glass GC vials, total volume being 1 mL. 1-pentanol was used as an internal standard in all samples to correct for any inconsistencies with injection volumes and GC performance from sample to sample. In the tables above, are GC data containing the peak areas manually integrated using the GC software provided by Shimadzu. Additionally, peak areas were converted to concentration (in g/L) using the peak areas of the 1 g/L standard as well as the ratio of the internal standards. The data represents the production of three strains in triplicate, all overexpressing alsS, ilvC, ilvD, and kivd. The average numbers of the three trials are also listed below along with the standard deviations. JCL260 ΔyqhD showed a marked increase in isobutyraldehyde production and reduced isobutanol as compared to JCL260. JCL260 ΔyqhD, ΔadhP, ΔeutG, ΔyiaY, and ΔyjgB produced even higher level of isobutyraldehyde and lower isobutanol. Also, listed in the table are the cell densities of the cultures after 24 hours recorded as the optical density at 600 nm (OD600).

TABLE 2

Gas Chromatography Data Analysis.

| | GC Peak Areas | | | | Concentrations (g/L) | | |
| --- | --- | --- | --- | --- | --- | --- | --- |
| Strain | Isobutyraldehyde | Ethanol | Isobutanol | (Int. STD)1-Pentanol | Isobutyraldehyde | Ethanol | Isobutanol |
| 1 g/L Standard | 1606375 | 1689731 | 2504551.5 | 2499249.7 | 10.0 | 10.0 | 10.0 |
| JCL260 #1 | 98490.6 | 131606.1 | 2873726.2 | 3079578.5 | 0.5 | 0.6 | 9.3 |
| JCL260 #2 | 77122.5 | 118846 | 3040802.3 | 3209332.2 | 0.4 | 0.5 | 9.5 |
| JCL260 #3 | 78626.5 | 126322 | 3078302.3 | 3189692.4 | 0.4 | 0.6 | 9.6 |
| JCL260ΔyqhD | 852212.6 | 14641.5 | 1182500.9 | 3178329.3 | 4.2 | 0.1 | 3.7 |
| JCL260ΔyqhD | 772220 | 18611.3 | 1205856.3 | 3199900.4 | 3.8 | 0.1 | 3.8 |
| JCL260ΔyqhD | 683198.5 | 21652.4 | 1175439.7 | 3186628.8 | 3.3 | 0.1 | 3.7 |
| JCL260 ΔyqhD, ΔadhP, ΔeutG, ΔyiaY, ΔyjgB | 1084541.7 | 104692.7 | 333832.3 | 3201334.4 | 5.3 | 0.5 | 1.0 |
| JCL260 ΔyqhD, ΔadhP, ΔeutG, ΔyiaY, ΔyjgB | 1081229.5 | 99231.6 | 303220.6 | 3243696.7 | 5.2 | 0.5 | 0.9 |
| JCL260 ΔyqhD, ΔadhP, ΔeutG, ΔyiaY, ΔyjgB | 984248.8 | 107456.6 | 311386 | 3273754.7 | 4.7 | 0.5 | 0.9 |

| | | Mean & STDEV | | | Mean |
| --- | --- | --- | --- | --- | --- |
| | | Isobutyraldehyde | Ethanol | Isobutanol | OD600 |
| JCL260 | Mean: | 0.4 | 0.6 | 9.5 | 4.9 |
| | Standard Deviation: | 0.07 | 0.04 | 0.16 | 1.05 |
| JCL260 ΔyqhD | Mean: | 3.8 | 0.1 | 3.7 | 4.6 |
| | Standard Deviation: | 0.42 | 0.02 | 0.04 | 0.10 |
| JCL260 ΔyqhD ΔadhP ΔeutG ΔyiaY ΔyjgB | Mean: | 5.0 | 0.5 | 1.0 | 4.5 |
| | Standard Deviation: | 0.32 | 0.02 | 0.06 | 0.64 |

Figure 10:
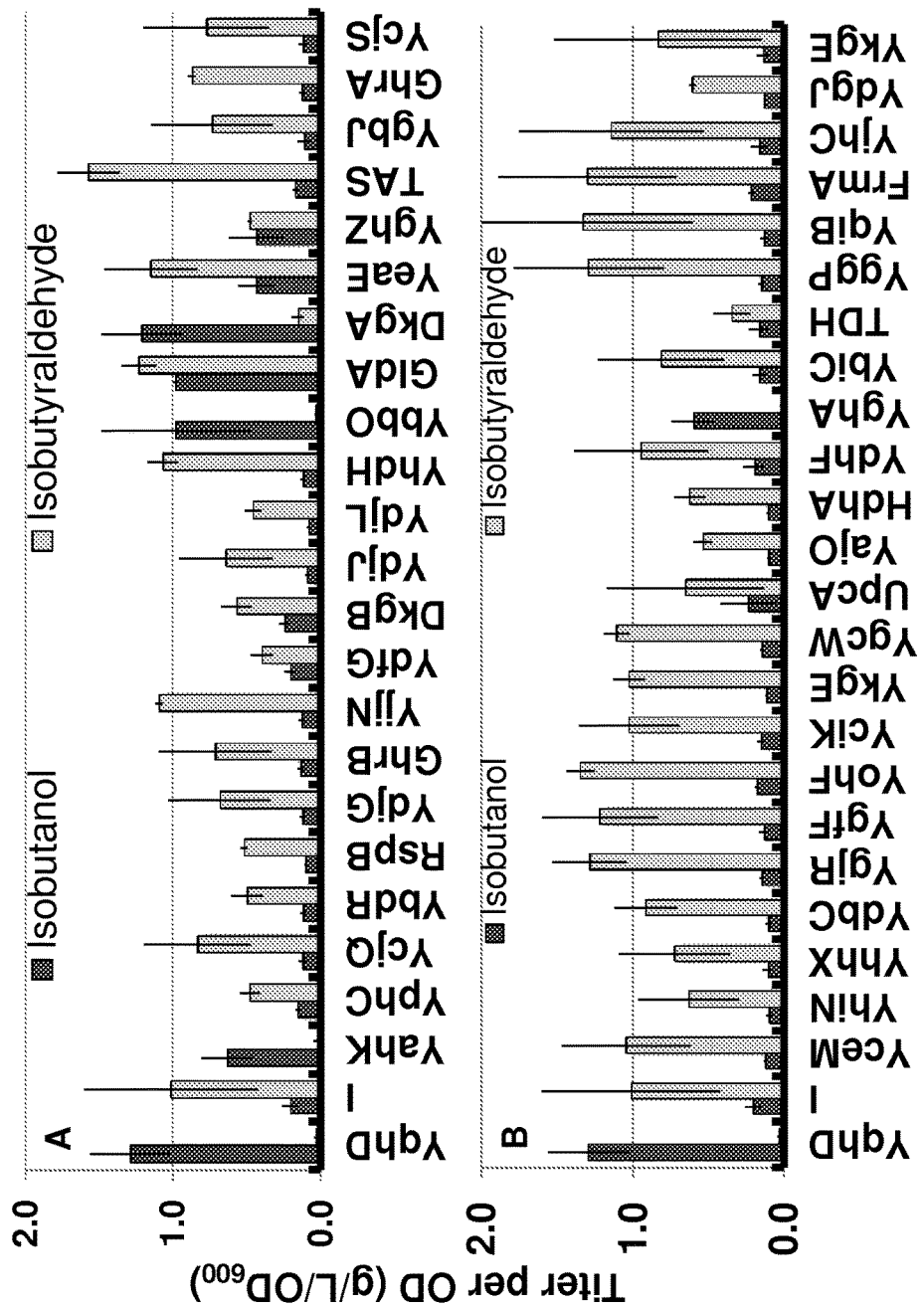
FIG. 10 illustrates the production of isobutyraldehyde and isobutanol by overexpression of each candidate aldehyde reductase gene. The gene overexpressed is labeled on the x-axis, and the amount of isobutanol and isobutyraldehyde produced is plotted on the y-axis. All experiments were conducted in *E. coli* strain AL626 (see Table 1) overexpressing alsS-ilvCD. A gene encoding a protein that has ALR activity will show high production of isobutanol and low production of isobutyraldehyde. According to these criteria, these results show that five out of the 44 genes tested encode proteins with ALR activity: yahK, ybbO, gldA, dkgA, and yghA. YqhD is included as a positive control.

Example 3: Engineering *E. coli* to Enhance Isobutyraldehyde and Reduce Isobutanol Production The strain described in the previous example, AL626, showed high isobutyraldehyde production and low isobutanol production. However, long-term production showed increasing isobutanol formation after a few days, indicative of residual aldehyde reductase (ALR) activity in *E. coli* (Rodriguez and Atsumi, Microb Cell Fact 2012, 11:90). To identify gene(s) responsible for this activity, 44 candidate alr genes were tested for their ability to produce isobutanol (FIG. 10). *E. coli* strain AL626 (Table 1), which overexpresses alsS-ilvCD and kivd-alr was used for production assays. Any candidate ALR that results in high production of isobutanol and low production of isobutyraldehyde was determined to possess ALR activity. Of the 44 candidate ALRs tested, five (YahK, YbbO, GldA, DkgA, and YghA) resulted in high isobutanol production, indicating that they are able to convert isobutyraldehyde to isobutanol (FIG. 10).

Figure 11:
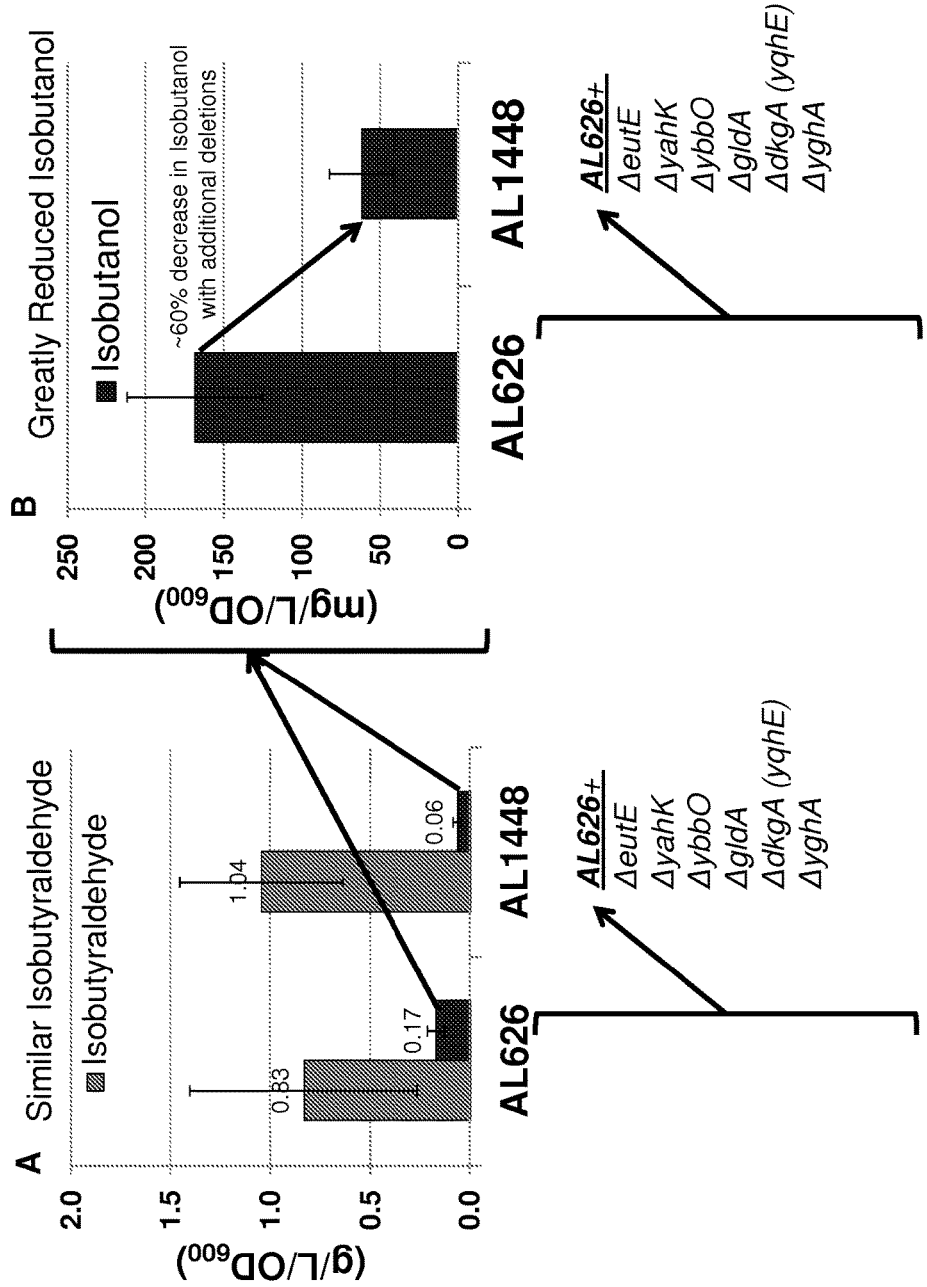
FIG. 11 illustrates the effect of mutating all five of the candidate ALR genes and eutE on isobutyraldehyde and isobutanol production. *E. coli* strain AL1448 is derived from AL626 but further contains deletion mutations of each of the listed genes.
Figure 12:
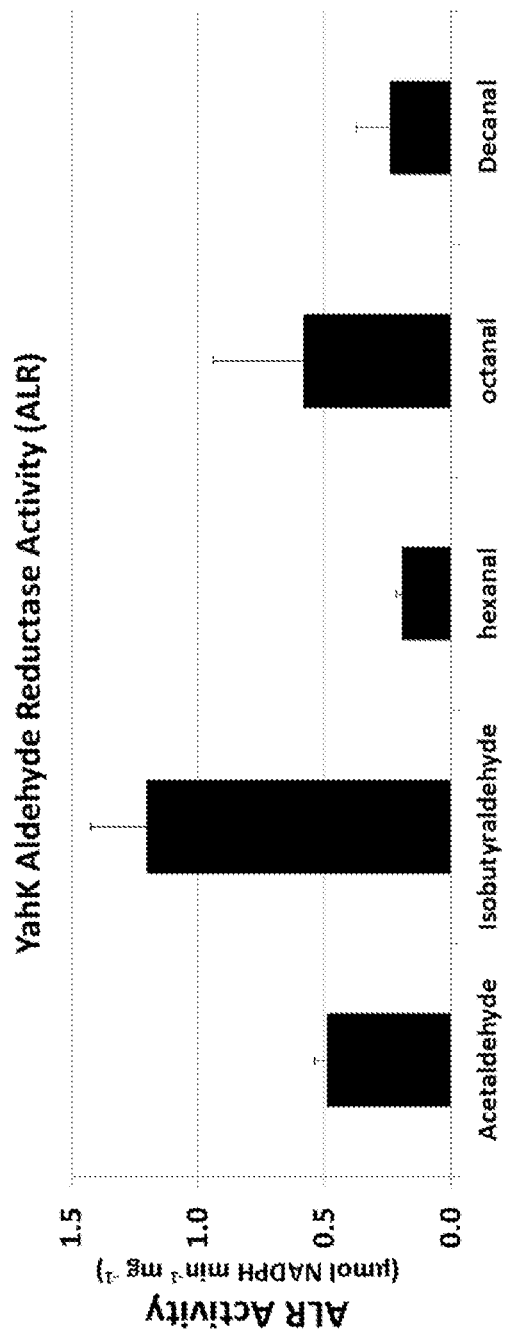
FIG. 12 shows the ALR activity of extracts made from *E. coli* strain AL626 overexpressing YahK on various substrates.
Figure 13:
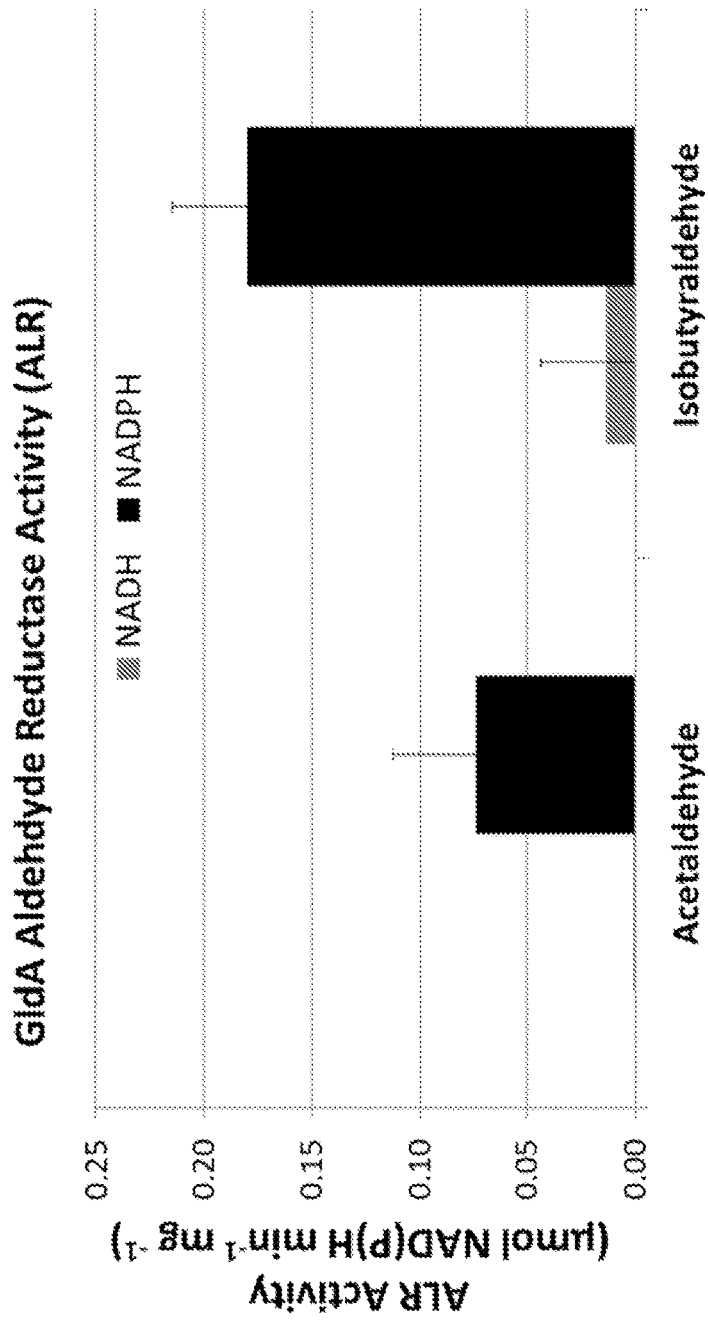
FIG. 13 shows the ALR activity of extracts made from *E. coli* strain AL626 overexpressing GldA on various substrates with NADH (grey bars) or NADPH (black bars) as cofactors.
Figure 14:
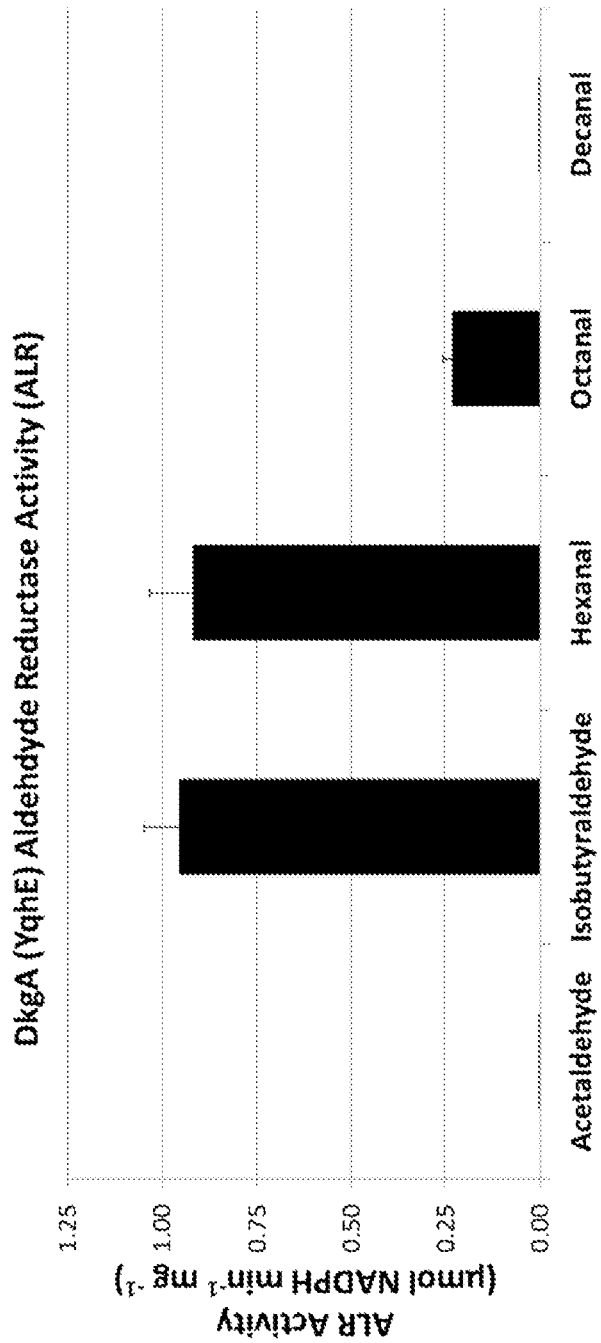
FIG. 14 shows the ALR activity of extracts made from *E. coli* strain AL626 overexpressing DkgA (YqhE) on various substrates.
Figure 15:
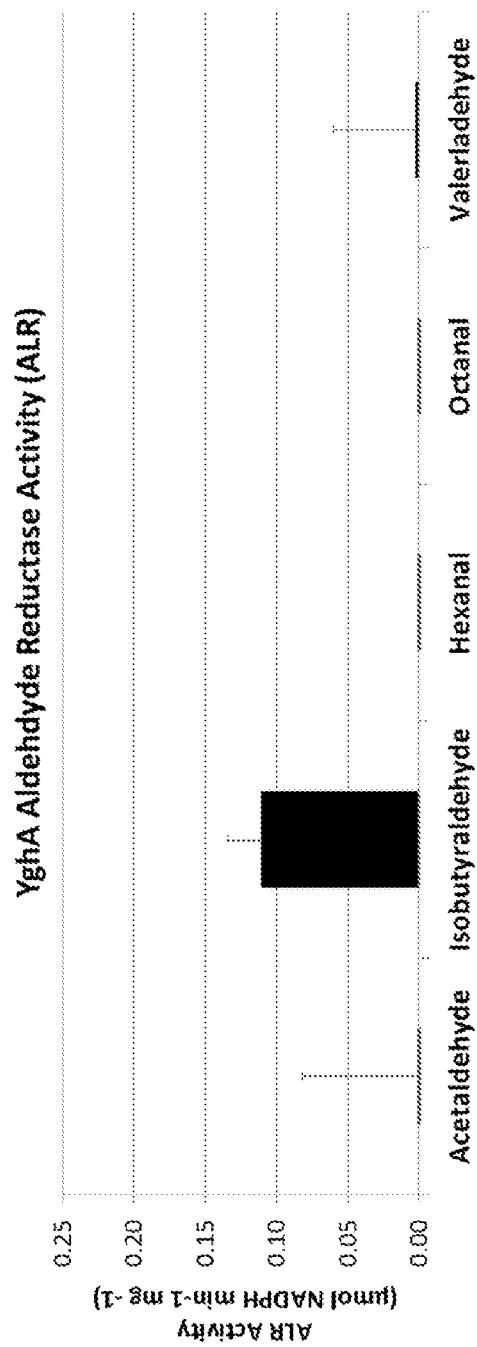
FIG. 15 shows the ALR activity of extracts made from *E. coli* strain AL626 overexpressing YghA on various substrates.
Figure 16:
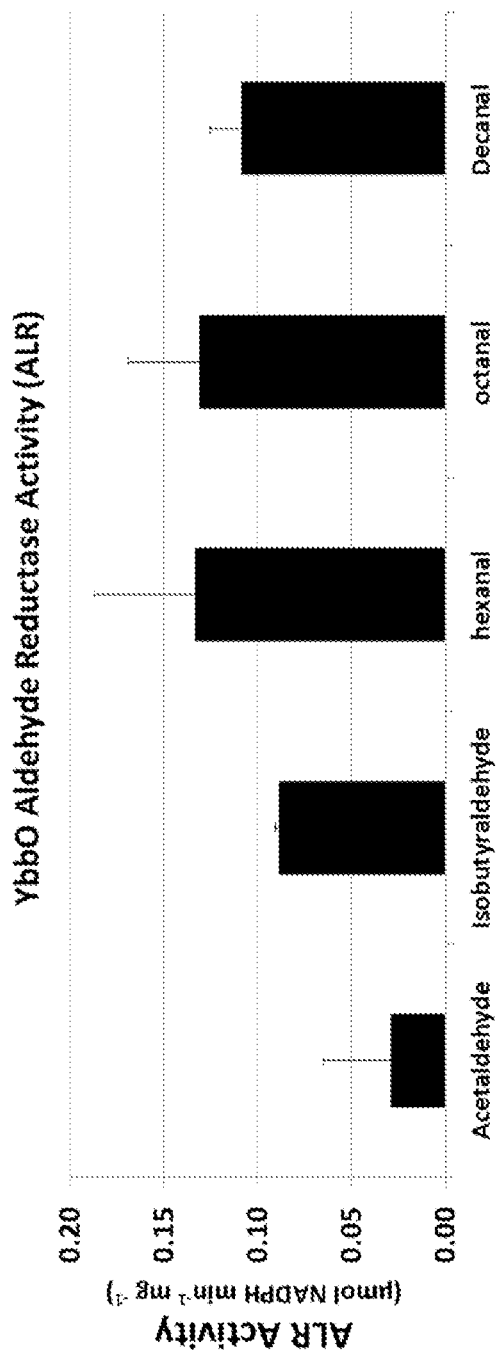
FIG. 16 shows the ALR activity of extracts made from *E. coli* strain AL626 overexpressing YbbO on various substrates.

To further reduce the production of isobutanol, *E. coli* strain AL626 was modified to include deletions of each of the newly identified alr genes (yahK, ybbO, gldA, dkgA/ yqhE, and yghA), resulting in strain AL1448 (Table 1). This led to a further a 60% reduction in isobutanol production in the first 24 hours, indicating that the enzymes encoded by these genes were contributing to isobutanol formation in *E. coli* (FIG. 11). The gene eutE was also deleted. This gene does not code for an aldehyde reductase, but rather an aldehyde dehydrogenase, and this deletion can be beneficial for isobutyraldehyde production.

To confirm the ALR activity of these newly defined alr genes, each gene was expressed in *E. coli* strain AL626, and extracts were tested for ALR activity. High copy (colE1) plasmids containing kivd-alr (yahK, gldA, dkgA, or yghA) operon under the IPTG inducible promoter PLlacO1 were introduced into AL626 (Rodriguez and Atsumi, Microb Cell Fact 2012, 11:90). AL626 has several alr deletions and thus has very low background activity, making it suitable for ALR/ADH enzyme assays. The ALR activities of each enzyme against selected aldehyde substrates are depicted in FIGS. 12-16. These results confirm that each newly defined alr gene possesses ALR activity.

For an isobutyraldehyde/isobutanol production test, 1% (vol/vol) of the overnight culture was inoculated in 5 mL production media in 15 mL screw-cap culture tubes and grown at 37° C. in a rotary shaker (250 RPM) until $OD_{600}$~0.4, then induced with 1 mM isopropyl-β-D-thiogalactoside (IPTG) and allowed to produce for 24 hours after induction. Screw-cap tubes were tightly sealed to prevent evaporation of isobutyraldehyde. Production media is defined as M9 medium containing 5 g/L yeast extract, 36 g/L glucose, and 1000-fold dilution of A5 trace metal mix (2.86 g $H_3BO_3$, 1.81 g $MnCl_2.4H_2O$, 0.222 g $ZnSO_4.7H_2O$, 0.39 g $Na_2MoO_4.2H_2O$, 0.079 g $CuSO_4.5H_2O$, 49.4 mg $Co(NO_3)_2.6H_2O$ per liter water). Concentrations of all products were analyzed by gas chromatography (GC) equipped with a flame ionization detector (FID). The GC system is a Shimadzu GC-2010 with an AOC-20 S auto sampler and AOC-20i Auto Injector. The column used was a DB-Wax capillary column (30 m length, 0.32-mm diameter, 0.50-μm film thickness) from Agilent Technologies. GC oven temperature was initially held at 40° C. for 3 minutes, then increased at a rate of 45° C. $min^{-1}$ until 235° C. and held for 3 min. Injector temperature was held at 225° C. and FID detector was held at 330° C. Injection volume was 0.5 μL, injected at a 15:1 split ratio. Helium was used as the carrier gas and 1-pentanol was used as an internal standard.

For ALR activity assays, the strains were grown to $OD_{600}$ value of ~0.4 in 5 mL LB medium at 37° C., followed by adding 1 mM IPTG. Protein overexpression was performed at 30° C. for 2 h. Then 1.8 mL of cells were centrifuged at 13,000 RPM for 10 minutes, resuspended in 300 μL BugBuster Protein Extraction Reagent (Novagen, San Diego, Calif.), and incubated at room temperature for 20 min for cell lysis. The samples were centrifuged for 20 min, 16,000 g, at 4° C. Supernatants were taken for enzyme assays. ADH activities were measured by following the reduction of aldehyde with NADH or NADPH at 340 nm at 37° C. using a Synergy H1 Hybrid Plate Reader from BioTek Instruments, Inc. (Winooski, Vt.). The assay mixture contained 25 mM aldehyde, 50 mM 3-(N-morpholino)propanesulfonic acid (MOPS) buffer (pH 7.0), 0.2 mM Tris-Cl (pH 7.00), 0.2 mM NAD(P)H, and 12.5 mM potassium phosphate buffer (pH 7.5). One unit of activity is defined as the oxidation of 1 μmol of NAD(P)H per minute per mg protein. Protein concentrations were measured using 5× Advanced Protein Assay Reagent (Cytoskeleton Inc., Denver, Colo.) by diluting 5 μL of cell extract in 1 mL of 1× Advanced Protein Assay Reagent and measuring the $OD_{590}$ of the mixture. Bovine serum albumin was used to prepare a standard curve.

We claim:

1. A genetically modified *Escherichia coli* (*E. coli*) comprising
   a recombinant nucleotide sequence encoding 2-keto-acid decarboxylase;
   a deletion in an eutE gene: and
   a mutation in each of genes set forth in group (a) or group (b):
   (a) adhE, yqhD, adhP, eutG, yiaY, and yjgB genes, wherein said mutation reduces alcohol dehydrogenase activity of products of said genes; or
   (b) adhE, yqhD, adhP, eutG, fucO, and yjgB genes, and wherein said mutation reduces isobutyraldehyde reductase activity of products of said genes.

2. The *E. coli* of claim 1, wherein said *E. coli* comprises a mutation in each of adhE, yqhD, adhP, eutG, yiaY, and yjgB genes, and wherein said mutation reduces alcohol dehydrogenase activity of products of said genes.

3. The *E. coli* of claim 1, wherein said *E. coli* comprises a mutation in each of adhE, yqhD, adhP, eutG, fucO, and yjgB genes, and wherein said mutation reduces isobutyraldehyde reductase activity of products of said genes.

4. The *E. coli* of claim 1, wherein said 2-keto-acid decarboxylase is Kivd.

5. The *E. coli* of claim 4, wherein said *E. coli* produces an increased level of a 2-keto-acid as compared to wild type *E. coli*.

6. The *E. coli* of claim 5, wherein said *E. coli* has elevated expression or activity of one or more of:
   a) acetohydroxy acid synthase or acetolactate synthase;
   b) acetohydroxy acid isomeroreductase; and
   c) dihydroxy-acid dehydratase;
   as compared to wild type *E. coli*.

7. The *E. coli* of claim 6, wherein said *E. coli* has elevated expression or activity of AlsS, IlvC, and IlvD as compared to wild type *E. coli*.

8. The *E. coli* of claim 7, further comprising a deletion in each of fnr, ldhA, frdBC, pflB, and pta genes.

9. The *E. coli* of claim 5, wherein the *E. coli* has elevated expression or activity of one or more of:
   a) α-isopropylmalate synthase;
   b) β-isopropylmalate dehydrogenase;
   c) α-isopropylmalate isomerase; and
   d) threonine dehydratase;
   as compared to wild type *E. coli*.

10. The *E. coli* of claim 9, wherein the *E. coli* has elevated expression or activity of LeuA, LeuCD, LeuB, and IlvA as compared to wild type *E. coli*.

11. The *E. coli* of claim 5, wherein the *E. coli* has elevated expression or activity of one or more of:
    a) threonine dehydratase;
    b) acetohydroxy acid synthase or acetolactate synthase;
    c) acetohydroxy acid isomeroreductase; and
    d) dihydroxy-acid dehydratase;
    as compared to wild type *E. coli*.

12. The *E. coli* of claim 11, wherein the *E. coli* has elevated expression or activity of IlvA, AlsS, IlvC, and IlvD as compared to wild type *E. coli*.

13. A method for producing an aldehyde, the method comprising:
    (a) providing the *E. coli* of claim 7;
    (b) culturing the *E. coli* of (a) in culture medium comprising a suitable substrate under conditions suitable for the conversion of the substrate to an aldehyde; and
    (c) substantially purifying the aldehyde.

14. The method of claim 13, wherein said step of purifying the aldehyde comprises:
 (i) bubbling air while culturing the *E. coli* to evaporate the aldehyde from the culture medium; and
 (ii) condensing the evaporated aldehyde.

15. The method of claim 14, wherein said step of condensing is done with a Graham condenser.

16. The method of claim 15, wherein the aldehyde comprises isobutyraldehyde, butyraldehyde, or propionaldehyde.

17. A method of producing an aldehyde, the method comprising:
 (a) providing the *E. coli* of claim 10;
 (b) culturing the *E. coli* of (a) in culture medium comprising a suitable substrate under conditions suitable for the conversion of the substrate to an aldehyde; and
 (c) substantially purifying the aldehyde.

18. A method for producing an aldehyde, the method comprising:
 (a) providing the *E. coli* of claim 12;
 (b) culturing the *E. coli* of (a) in culture medium comprising a suitable substrate under conditions suitable for the conversion of the substrate to an aldehyde; and
 (c) substantially purifying the aldehyde.

* * * * *